(12) United States Patent
Janzen et al.

(10) Patent No.: US 11,485,994 B2
(45) Date of Patent: *Nov. 1, 2022

(54) METHODS AND SYSTEMS FOR USING ENCAPSULATED MICROBUBBLES TO PROCESS BIOLOGICAL SAMPLES

(71) Applicant: The University of North Carolina at Chapel Hill, Chapel Hill, NC (US)

(72) Inventors: William Perry Janzen, Chapel Hill, NC (US); Samantha Gail Pattenden, Mebane, NC (US); Chatura Nadisha Jayakody, Morrisville, NC (US); Jason Eric Streeter, Chapel Hill, NC (US); Paul Alexander Dayton, Carrboro, NC (US); Cameron Champion Wood, Raleigh, NC (US); Siddharth Kaup Shenoy, Durham, NC (US)

(73) Assignee: THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 94 days.

This patent is subject to a terminal disclaimer.

(21) Appl. No.: 15/990,171

(22) Filed: May 25, 2018

(65) Prior Publication Data

US 2018/0274008 A1    Sep. 27, 2018

Related U.S. Application Data

(62) Division of application No. 14/432,747, filed as application No. PCT/US2013/063397 on Oct. 4, 2013, now Pat. No. 9,982,290.

(60) Provisional application No. 61/709,488, filed on Oct. 4, 2012.

(51) Int. Cl.
    *C12Q 1/6806*     (2018.01)
    *C12N 15/10*     (2006.01)
    *G01N 1/38*     (2006.01)

(52) U.S. Cl.
CPC ........... *C12Q 1/6806* (2013.01); *C12N 15/10* (2013.01); *C12N 15/1003* (2013.01); *G01N 1/38* (2013.01); *G01N 2001/387* (2013.01)

(58) Field of Classification Search
CPC .. C12Q 1/6806; C12N 15/10; C12N 15/1003; G01N 1/38; G01N 2001/387
See application file for complete search history.

(56) References Cited

U.S. PATENT DOCUMENTS

| | | | |
|---|---|---|---|
| 4,423,153 A * | 12/1983 | Ranney | C12Q 1/68 435/6.16 |
| 4,870,953 A | 10/1989 | DonMicheal et al. | |
| 4,957,656 A | 9/1990 | Cerny et al. | |
| 5,254,112 A | 10/1993 | Sinofsky et al. | |
| 5,380,411 A * | 1/1995 | Schlief | A61K 49/223 204/157.15 |
| 5,469,854 A | 11/1995 | Unger | |
| 5,558,853 A | 9/1996 | Quay | |
| 5,585,112 A | 12/1996 | Unger et al. | |
| 5,716,597 A | 2/1998 | Lohrmann et al. | |
| 5,730,955 A | 3/1998 | Lohrmann | |
| 5,735,811 A | 4/1998 | Brisken | |
| 5,740,596 A | 4/1998 | Corl et al. | |
| 5,840,276 A | 11/1998 | Apfel | |
| 5,879,303 A | 3/1999 | Averkiou et al. | |
| 5,906,580 A | 5/1999 | Kline-Schoder et al. | |
| 6,024,718 A | 2/2000 | Chen et al. | |
| 6,033,645 A | 3/2000 | Unger et al. | |
| 6,071,495 A | 6/2000 | Unger et al. | |
| 6,312,383 B1 | 11/2001 | Lizzi et al. | |
| 6,371,917 B1 | 4/2002 | Ferrara et al. | |
| 6,398,792 B1 | 6/2002 | O'Connor | |
| 6,409,667 B1 | 6/2002 | Hossack | |
| 6,740,039 B1 | 5/2004 | Rafter et al. | |
| 7,358,226 B2 | 4/2008 | Dayton et al. | |
| 9,427,410 B2 | 8/2016 | Dayton et al. | |
| 9,532,769 B2 | 1/2017 | Dayton et al. | |
| 9,982,290 B2 | 5/2018 | Janzen et al. | |
| 10,493,038 B2 | 12/2019 | Dayton et al. | |
| 11,123,302 B2 | 9/2021 | Dayton et al. | |

(Continued)

FOREIGN PATENT DOCUMENTS

| | | |
|---|---|---|
| CA | 2 773 181 | 2/2018 |
| EP | 1 073 716 B1 | 4/2004 |

(Continued)

OTHER PUBLICATIONS

Ward, M et al. Ultrasound-induced cell lysis and sonoporation enhanced by contrast agents. J. Acoust. Soc. Am. 1999. 105(5): 2951-2957. (Year: 1999).*

Non-Final Office Action for U.S. Appl. No. 15/035,211 (dated Feb. 9, 2018).

Commonly-assigned, co-pending U.S. Appl. No. 15/880,481 for "Formulation of Acoustically Activatable Particles Having Low Vaporization Energy and Methods for Using Same," (Filed Jan. 25, 2018).

Notice of Allowance and Fee(s) Due and Examiner Initiated Interview Summary for U.S. Appl. No. 14/432,747 (dated Jan. 10, 2018).

(Continued)

*Primary Examiner* — Renee Claytor
*Assistant Examiner* — Susan E. Fernandez
(74) *Attorney, Agent, or Firm* — Jenkins, Wilson, Taylor & Hunt, P.A.

(57) ABSTRACT

Methods and systems for using encapsulated microbubbles to process biological samples are disclosed. According to one aspect, a method for using encapsulated microbubbles to process a biological sample includes creating a mixture comprising encapsulated microbubbles mixed with a biological sample and adding activation energy to the mixture to cause at least some of the microbubbles to oscillate or burst and thereby process the sample, including effecting cell lysis, shearing DNA, and/or performing tissue dispersion.

21 Claims, 8 Drawing Sheets

(56) References Cited

U.S. PATENT DOCUMENTS

| | | |
|---|---|---|
| 2001/0019710 A1 | 9/2001 | Berg et al. |
| 2001/0028893 A1 | 10/2001 | Spears |
| 2002/0045890 A1 | 4/2002 | Celliers et al. |
| 2002/0099290 A1 | 7/2002 | Haddad |
| 2003/0165431 A1 | 9/2003 | Pines et al. |
| 2005/0014203 A1* | 1/2005 | Darfler ............... C12Q 1/37 435/7.2 |
| 2005/0038423 A1 | 2/2005 | Makin et al. |
| 2005/0084538 A1 | 4/2005 | Dayton et al. |
| 2006/0078501 A1 | 4/2006 | Goertz et al. |
| 2007/0035204 A1 | 2/2007 | Angelsen et al. |
| 2007/0178047 A1 | 8/2007 | Kawabata |
| 2007/0292495 A1 | 12/2007 | Ludwig et al. |
| 2008/0182237 A1 | 7/2008 | Bentwich et al. |
| 2008/0208044 A1 | 8/2008 | Lecoq et al. |
| 2008/0311046 A1 | 12/2008 | Kawabata et al. |
| 2008/0312535 A1 | 12/2008 | Kawabata |
| 2009/0023597 A1 | 1/2009 | Wong et al. |
| 2009/0076394 A1 | 3/2009 | Wong et al. |
| 2009/0117177 A1 | 5/2009 | Rapoport et al. |
| 2009/0182237 A1 | 7/2009 | Bjorn et al. |
| 2009/0317884 A1 | 12/2009 | Laugharn, Jr. |
| 2010/0009424 A1 | 1/2010 | Forde et al. |
| 2010/0224782 A1 | 9/2010 | Pan et al. |
| 2010/0331686 A1 | 12/2010 | Hossack et al. |
| 2011/0044903 A1 | 2/2011 | Borrelli |
| 2012/0172720 A1 | 7/2012 | Asami |
| 2012/0203103 A1 | 8/2012 | Wang et al. |
| 2012/0209116 A1 | 8/2012 | Hossack et al. |
| 2012/0220869 A1 | 8/2012 | Dayton et al. |
| 2012/0270177 A1 | 10/2012 | Nakashima et al. |
| 2013/0053691 A1 | 2/2013 | Kawabata et al. |
| 2013/0336891 A1 | 12/2013 | Dayton et al. |
| 2014/0242584 A1* | 8/2014 | Ji ............... C12N 15/1003 435/6.11 |
| 2015/0252355 A1 | 9/2015 | Janzen et al. |
| 2016/0262727 A1 | 9/2016 | Dayton et al. |
| 2018/0221515 A1 | 8/2018 | Dayton et al. |
| 2020/0405258 A1 | 12/2020 | Dayton et al. |
| 2021/0007759 A1 | 1/2021 | Jiang et al. |
| 2021/0267614 A1 | 9/2021 | Jiang et al. |
| 2022/0000790 A1 | 1/2022 | Dayton et al. |

FOREIGN PATENT DOCUMENTS

| | | | |
|---|---|---|---|
| WO | WO 2011/029094 A2 | 3/2011 | |
| WO | WO 2011/074268 A1 | 6/2011 | |
| WO | WO 2011/149985 A1 | 12/2011 | |
| WO | WO 2012/048335 A2 | 4/2012 | |
| WO | WO 2014/055832 A1 | 4/2014 | |
| WO | WO 2015/070186 A1 | 5/2015 | |
| WO | WO 2016/118947 A1 | 7/2016 | |

OTHER PUBLICATIONS

Applicant Initiated Interview Summary for U.S. Appl. No. 14/432,747 (dated Jul. 24, 2017).
Notice of Allowance for Canadian Patent Application No. 2,773,181 (dated Jul. 10, 2017).
Final Office Action for U.S. Appl. No. 14/432,747 (dated May 19, 2017).
Applicant-Initiated Interview Summary for U.S. Appl. No. 14/432,747 (dated Feb. 22, 2017).
Non-Final Office Action for U.S. Appl. No. 14/432,747 (dated Oct. 12, 2016).
Office Action for Canadian Patent Application No. 2,773,181 (dated Sep. 12, 2016).
Commonly-assigned, co-pending U.S. Appl. No. 15/247,840 for "Formulation of Acoustically Activatable Particles Having Low Vaporization Energy and Methods for Using Same," (Filed Aug. 25, 2016).
Notice of Allowance and Fee(s) Due for U.S. Appl. No. 13/393,500 (dated Aug. 22, 2016).
Notification of Transmittal of the International Search Report and the Written Opinion of the International Searching Authority, or the Declaration for International Application No. PCT/US2016/014685 (dated Jun. 30, 2016).
Applicant-Initiated Interview Summary for U.S. Appl. No. 13/393,500 (dated Jun. 21, 2016).
Restriction/Election Requirement for U.S. Appl. No. 14/432,747 (dated Jun. 3, 2016).
Notice of Allowance, Examiner-Initiated Interview Summary, and AFCP 2.0 Decision for U.S. Appl. No. 13/876,165 (dated Apr. 28, 2016).
Applicant-Initiated Interview Summary for U.S. Appl. No. 13/876,165 (dated Mar. 28, 2016).
Final Office Action for U.S. Appl. No. 13/393,500 (dated Feb. 24, 2016).
Commonly-assigned, co-pending PCT International Patent Application No. PCT/US2016/014685 for "Apparatuses, Systems, and Methods for Preclinical Ultrasound Imaging of Subjects," (Filed Jan. 25, 2016).
Final Office Action for U.S. Appl. No. 13/876,165 (dated Dec. 31, 2015).
Applicant-Initiated Interview Summary for U.S. Appl. No. 13/393,500 (dated Nov. 16, 2015).
Non-Final Office Action for U.S. Appl. No. 13/393,500 (dated Jul. 9, 2015).
Non-Final Office Action for U.S. Appl. No. 13/876,165 (dated Jun. 10, 2015).
Notification of Transmittal of the International Search Report and the Written Opinion of the International Searching Authority, or the Declaration for PCT International Application No. PCT/US2014/064889 (dated Apr. 2, 2015).
Restriction and/or Election Requirement for U.S. Appl. No. 13/393,500 (dated Jan. 27, 2015).
Restriction and/or Election Requireement for U.S. Appl. No. 13/876,165 (dated Dec. 1, 2014).
Notification of Transmittal of the International Search Report and the Written Opinion of the International Searching Authority, or the Declaration for PCT International Application No. PCT/US2013/063397 (dated Jan. 16, 2014).
Notification of Transmittal of the International Search Report and the Written Opinion of the International Searching Authority, or the Declaration for International Application No. PCT/US2011/055713 (dated May 18, 2012).
Notification of Transmittal of the International Search Report and the Written Opinion of the International Searching Authority, or the Declaration for International Patent Application No. PCT/US2010/047988 (dated Mar. 31, 2011).
Ainslie et al., "Review of scattering and extinction cross-sections, damping factors, and resonance frequencies of a spherical gas bubble," The Journal of the Acoustical Society of America, vol. 130, pp. 3184-3208 (2011).
Alexandridis et al., "Surface Activity of Poly(ethylene oxide)-block-Poly(propylene oxide)-block-Poly(ethylene oxide) Copolymers," Langmuir, vol. 10, pp. 2604-2612 (1994).
Allen et al., "Effect of Coupled Oscillations on Microbubble Behavior," The Journal of the Acoustical Society of America, vol. 14, No. 3, pp. 1678-1690 (Sep. 2003).
Allen, "Liposomes—Opportunities in Drug Delivery," Drugs, vol. 54, Suppl. 4, pp. 8-14 (1997).
Anderson et al., "Ultrasound Molecular Imaging of Tumor Angiogenesis with an Integrin Targeted Microbubble Contrast Agent," Invest Radiol, vol. 46, No. 4, pp. 1-21 (Apr. 2011).
Anderson, "Shotgun DNA Sequencing Using Cloned DNase I-generated Fragments," Nucleic Acids Research, vol. 9, No. 13, pp. 3015-3027 (Jul. 1981).
Aparicio et al., "Chromatin Immunoprecipiation for Determining the Association of Proteins with Specific Genomic Sequences in Vivo," Current Protocols in Cell Biology, Chapter 17, Unit 17.7, pp. 17.7.1-17.7.23 (2004).
Apfel, "Activatable infusable dispersions containing drops of a superheated liquid for methods of therapy and diagnosis," (1998).

(56) References Cited

OTHER PUBLICATIONS

Asami et al., "Acoustic Signal Characterization of Phase Change Nanadroplets in Tissue-Mimicking Phantom Gels," Jpn. J. Appl. Phys., vol. 49 (2010).
Asami et al., "Repeatable vaporization of optically vaporizable perfluorocarbon droplets for photoacoustic contrast enhanced imaging," 2012 IEEE International Ultrasonics Symposium (IUS), pp. 1200-1203 (2012).
Auton et al., "The Force Exerted on a Body in an Inviscid Unsteady Non-Uniform Rotational Flow," J. Fluid Mech., vol. 197, pp. 241-257 (1988).
Behm et al., "Cellular and Molecular Imaging with Targeted Contrast Ultrasound," Ultrasound Quarterly, vol. 22, No. 1, pp. 67-72 (Mar. 2006).
Bekeredjian et al., "Therapeutic Use of Ultrasound Targeted Microbubble Destruction: A Review of Non-Cardiac Applications," Ultraschall in Med, vol. 27, pp. 134-140 (2006).
Bekeredjian et al., "Ultrasound-targeted Microbubble Destruction Can Repeatedly Direct Highly Specific Plasmid Expression to the Heart," Circulation—Journal of the American Heart Association, vol. 108, pp. 1022-1026 (2003).
Bernasconi et al., "A Chemogenomic Analysis of the Human Proteome: Application to Enzyme Families," Journal of Biomolecular Screening, vol. 12, No. 7, pp. 972-982 (2007).
Bloch et al., "Targeted Imaging Using Ultrasound Contrast Agents," IEEE Engineering in Medicine and Biology, vol. 23, No. 5, pp. 18-29 (Sep./Oct. 2004).
Böhmer et al., "Preparation of Monodisperse Polymer Particles and Capsules By Ink-Jet Printing," Colloids and Surfaces A: Physicochem. Eng. Aspects, vol. 289, pp. 96-104 (2006).
Borden et al., "A Stimulus-Responsive Contrast Agent for Ultrasound Molecular Imaging," Biomaterials, vol. 29, No. 5, pp. 1-19 (Feb. 2008).
Borden et al., "Ultrasound Radiation Force Modulates Ligand Availability on Targeted Contrast Agents," Molecular Imaging, vol. 5, No. 3, pp. 139-147 (Jul. 2006).
Borden et al., "Influence of Lipid Shell Physicochemical Properties on Ultrasound-Induced Microbubble Destruction," IEEE Transactions on Ultrasonics, Ferroelectrics, and Frequency Control, vol. 52, No. 11, pp. 1992-2002 (Nov. 2005).
Borden et al., "Surface Phase Behavior and Microstructure of Lipid/PEG-Emulsifier Monolayer-Coated Microbubbles," Colloids and Surfaces B: Biointerfaces, vol. 35, pp. 209-223 (Mar. 2004).
Borden et al., "Dissolution Behavior of Lipid Monolayer-Coated, Air-Filled Microbubbles: Effect of Lipid Hydrophobic Chain Length," Langmuir, vol. 18, pp. 9225-9233 (2002).
Bouakaz et al., "Contrast Superharmonic Imaging: A Feasability Study," Ultrasound in Med. & Biol., vol. 29, No. 4, pp. 547-553 (2003).
Bouakaz et al., "Super Harmonic Imaging: A New Imaging Technique for Improved Contrast Detection," Ultrasound in Med.& Biol., vol. 28, No. 1, pp. 59-68 (2002).
Brennen, "Cavitation and Bubble Dynamics," Oxford University Press (1995).
Burger et al., "Sequencing Complete Mitochondrial and Plastid Genomes," Nature Protocols, vol. 2, No. 3, pp. 603-614 (Mar. 22, 2007).
Burns et al., "Microbubble Contrast for Radiological Imaging: 1. Principles," Ultrasound Quarterly, vol. 22, No. 1, pp. 5-13 (Mar. 2006).
Calderon et al., "A boundary element model of the ransport of a semi-infinite bubble through a microvessel birfurcation," Physics of Fluids, vol. 22, p. 11 (2010).
Campbell, "Tumor Physiology and Delivery of Nanopharmaceuticals," Anti-Cancer Agents in Medicinal Chemistry, vol. 6, No. 6, pp. 503-512 (2006).
Carson et al., "Acoustic Droplet Vaporization," http://www.ultrasound.med.umich.edu/Projects/ADV.html, pp. 1-4 (Downloaded from the Internet Mar. 17, 2015).

Caskey et al., "Direct Observations of Ultrasound Microbubble Contrast Agent Interaction with the Microvessel Wall," The Journal of the Acoustical Society of America, vol. 122, No. 2, pp. 1191-1200 (Aug. 2007).
Chatterjee et al., "A Newtonian Rheological Model for the Interface of Microbubble Contrast Agents," Ultrasound in Med. & Biol., vol. 29, No. 12, pp. 1749-1757 (Jul. 2003).
Chen et al., "Efficient Gene Delivery to Pancreatic Islets with Ultrasonic Microbubble Destruction Techology," PNAS, vol. 103, No. 22, pp. 8469-8474 (May 30, 2006).
Chen et al., "Multiple Acoustical Matching Layer Design of Ultrasonic Transducer for Medical Application," Jpn. J. Appl. Phys., vol. 41, pp. 6098-6107 (Oct. 2002).
Choi et al., "Spatio-Temporal Analysis of Molecular Delivery Through the Blood-Brain Barrier Using Focusing Ultrasound," Physics in Medicine and Biology, vol. 52, pp. 5509-5530 (2007).
Choi et al., "Spatiotemporal evolution of cavitation dynamics exhibited by flowing microbubbles during ultrasound exposure," The Journal of te Acoustical Society of America, vol. 132, pp. 3538-3549 (2012).
Choi et al., "Noninvasive, Transcranial and Localized Opening of the Blood-Brain Barrier Using Focused Ultrasound in Mice," Ultrasound in Medicine and Biology, vol. 33, No. 1, pp. 95-104 (2007).
Chomas et al., "Threshold of Fragmentation for Ultrasonic Contrast Agents," Journal of Biomedical Optics, vol. 6, No. 2, pp. 141-150 (Apr. 2001).
Chomas et al., "Mechanisms of Contrast Agent Destruction," IEEE Transactions Ultrasonics, Ferroelectrics, and Frequency Control, vol. 48, No. 1, pp. 232-248 (Jan. 2001).
Chomas et al., "Optical Observation of Contrast Agent Destruction," Applied Physics Letters, vol. 77, No. 7, pp. 1056-1058 (Aug. 14, 2000).
Chopra et al., "Multifrequency Ultrasound Transducers for Conformal Interstitial Thermal Therapy," IEEE Transactions on Ultrasonics, Ferroelectrics, and Frequency Control, vol. 50, No. 7, pp. 881-889 (Jul. 2003).
Clarke et al., "Production of harmonics in vitro by high-intensity focused ultrasound," Ultrasound in Medicine Biology, vol. 25, pp. 1417-1424 (1999).
Coakley et al., "Ultrasonic Manipulation of Particles and Cells," Bioseparation, vol. 4, pp. 73-83 (1994).
Coussios et al., "Applications of acoustics and cavitation to non-invasive therapy and drug delivery," Annual Review of Fluid Mechanics, vol. 40, pp. 395-420 (2008).
Couture et al., "Ultrasound inernal tattooing," Medical Physics, vol. 38, pp. 1116-1123 (2011).
Couture et al., "A Model for Reflectivity Enhancement Due to Surface Bound Submicrometer Particles," Ultrasound in Medicine & Biology, vol. 32, No. 8, pp. 1247-1255 (May 2006).
Couture et al., "Investigating Perfluorohexane Particles with High-frequency Ultrasound," Ultrasound in Medicine & Biology, vol. 32, No. 1, pp. 73-82 (Sep. 2005).
Cronin et al., "Comprehensive Next-Generation Cancer Genome Sequencing in the Era of Targeted Therapy and Personalized Oncology," Biomarkers Med.; 5(3), pp. 293-305 (2011).
Crowder et al., "Sonic Activation of Molecularly-Targeted Nanoparticles Accelerates Transmembrane Lipid Delivery to Cancer Cells Through Contact-mediated Mechanisms: Implications for Enhanced Local Drug Delivery," Ultrasound in Medicine & Biology, vol. 31, No. 12, pp. 1693-1700 (2005).
Crum, Lawrence A., "Bjerknes Forces on Bubbles in a Stationary Sound Field," The Journal of the Acoustical Society of America, vol. 57, No. 6, Part 1, pp. 1363-1370 (1975).
Crum et al., "The Motion of Bubbles in a Stationary Sound Field," The Journal of the Acoustical Society of America, p. 1411 (1969).
Culp et al., "Successful Microbubble Sonothrombolysis Without Tissue Plasminogen Activator in a Rabbit Model of Acute Ischemic Stroke," Stroke, vol. 42, No. 8, pp. 1-15 (Aug. 2011).
D'Astous et al., "Frequency dependence of ultrasound attenuation and backscatter in breast tissue," Ultrasound in Medicine Biology, vol. 12, pp. 795-808 (1986).

(56) References Cited

OTHER PUBLICATIONS

Dayton et al., "Molecular ultrasound imaging using microbubble contrast agents," Frontiers in Bioscience, vol. 12, pp. 5124-5142 (Sep. 1, 2007).
Dayton et al., "Application of Ultrasound to Selectively Localize Nanodroplets for Targeted Imaging and Therapy," Molecular Imaging, vol. 5, No. 3, pp. 1-32 (Jul. 2006).
Dayton et al., "Ultrasound-Mediated Therapies Using Oil and Perfluorocarbon-Filled Nanodroplets," Drug Development Research, vol. 67, pp. 42-46 (2006).
Dayton et al., "Ultrasonic Analysis of Peptide-and Antibody-Targeted Microbubble Contrast Agents for Molecular Imaging of αvβ3-expressing Cells," Molecular Imaging, vol. 3, No. 2, pp. 1-18 (Apr. 2004).
Dayton et al., "Targeted Imaging Using Ultrasound," Journal of Magnetic Resonance Imaging, vol. 16, pp. 362-377 (2002).
Dayton et al., "The Magnitude of Radiation Force on Ultrasound Contrast Agents," The Journal of the Acoustical Society of America, vol. 112, No. 5, Part 1, pp. 2183-2192 (2002).
Dayton et al., "Optical and Acoustical Dynamics of Microbubble Contrast Agents Inside Neutrophils," Biophysical Journal, vol. 80, pp. 1547-1556 (Mar. 2001).
Dayton et al., "Acoustic Radiation Force in Vivo: A Mechanism to Assist Targeting of Microbubbles," Ultrasound in Med. and Biol. vol. 25, No. 8, pp. 1195-1201 (1999).
Dayton et al., "Optical and Acoustical Observations of the Effects of Ultrasound on Contrast Agents," IEEE Transactions on Ultrasonics, Ferroelectronics, and Frequency Control, vol. 46, No. 1, pp. 220-232 (Jan. 1999).
Dayton et al., "A Preliminary Evaluation of the Effects of Primary and Secondary Radiation Forces on Acoustic Contrast Agents," IEEE Transactions on Ultrasonics, Ferroelectrics, and Frequency Control, vol. 44, No. 6, pp. 1264-1277 (Nov. 1997).
Dayton et al., "Action of Microbubbles When Insonified: Experimental Evidence," IEEE Ultrasonics Symposium, vol. 2, pp. 1131-1134 (1996).
Deininger, "Random Subcloning of Sonicated DNA: Application to Shotgun DNA Seuquence Analysis," Analytical Biochemistry, vol. 129(1), pp. 216-223 (1983).
Deng et al., "Ultrasound-Induced Cell Membrane Porosity," Ultrasound in Medicine & Biology, vol. 30, No. 4, pp. 519-526 (2004).
Desilets et al., "Design of Efficient Broad-Band Piezoelectric Transducers," IEEE Transactions on Sonics and Ultrasonics, vol. SU-25, No. 3, pp. 115-125 (May 1978).
Doinikov et al., "Review of shell models for contrast agent microbubbles," IEEE Trans. Ultrason. Ferroelectr. Freq. Control, vol. 58, pp. 981-993 (2011).
Doinikov et al., "Modeling of Nonlinear Viscous Stress in Encapsulating Shells of Lipid-Coated Contrast Agent Microbubbles," Ultrasonics, vol. 49, No. 2, pp. 1-17 (Feb. 2009).
Doinikov et al., "Resonance Frequencies of Lipid-Shelled Microbubbles in the Regime of Nonlinear Oscillations," Ultrasonics, vol. 49, No. 2, pp. 1-16 (Feb. 2009).
Doinikov et al., "Modeling of the Acoustic Response From Contrast Agent Microbubbles Near a Rigid Wall," Ultrasonics, vol. 49, No. 2, pp. 1-17 (Feb. 2009).
Doinikov et al., "Maxwell Rheological Model for Lipid-Shelled Ultrasound Microbubble Contrast Agents," The Journal fo the Acoustical Society of America, vol. 121, No. 6, pp. 1-26 (Jun. 2007).
Doinikov et al., "Spatio-temporal Dynamics of an Encapsulated Gas Bubble in an Ultrasound Field," The Journal of the Acoustical Society of America, vol. 120, No. 2, pp. 1-25 (Aug. 2006).
Dromi et al., "Pulsed-High Intensity Focused Ultrasound and Low Temperature Sensitive Liposomes for Enhanced Targeted Drug Delivery and Antitumor Effect," Clinical Cancer Research, vol. 13, pp. 2722-2727 (2007).
Ellegala et al., "Imaging Tumore Angiogenesis with Contrast Ultrasound and Microbubbles Targeted to αvγ3," Circulation, Journal of the American Heart Association, vol. 108 pp. 336-341 (2003).

Eshpuniyani et al., "A boundary element model of microbubble sticking and sliding in the microcirculation," International Journal of Heat and Mass Transfer, vol. 51, pp. 5700-5711 (2008).
Evans et al., "Physical Properties of Phase-Change Emulsions," Langmuir, vol. 22, pp. 9538-9545 (Sep. 2006).
Fabiilli et al., "Delivery of Chlorambucil Using an Acoustically triggered Perfluoropentane Emulsion," Ultrasound in Medicine and Biology, vol. 36, No. 8, pp. 1-25 (Aug. 2010).
Fabiilli et al., "Delivery of Water-Soluble Drugs Using Acoustically Triggered Perfluorocarbon Double Emulsions," Pharm. Res., vol. 27, No. 12, pp. 1-25 (Dec. 2010).
Fabiilli et al., "The Role of Inertial Cavitation in Acoustic Droplet Vaporization," IEEE Transactions on Ultrasonics, Ferroelectrics, and Frequency Control, vol. 56, No. 5, pp. 1-24 (May 2009).
Farook et al., "Controlling Size and Size Distribution of Electrohydrodynamically Prepared Microbubbles," Bubble Science, Engineering and Technology, vol. 1, No. 1/2, pp. 53-57 (2009).
Farook et al., "Preparation of Suspensions of Phospholipid-coated Microbubbles by Coaxial Electrohydrodynamic Atomization," The Journal of the Royal Society Interface, vol. 6, (32), pp. 271-277 (Jul. 2008).
Ferrara, "Driving Delivery Vehicles with Ultrasound," Advanced Drug Delivery Reviews, vol. 60, No. 10, pp. 1-9 (Jun. 30, 2008).
Ferrara et al., "Ultrasound Microbubble Contrast Agents: Fundamentals and Application to Gene and Drug Delivery," The Annual Review of Biomedical Engineering, vol. 9, pp. 415-447 (2007).
Ferretti et al., "Tumor Interstitial Fluid Pressure as an Early-Response Marker for Anticancer Therapeutics," Neoplasia, vol. 11, No. 9, pp. 874-881 (Sep. 2009).
Feshitan et al., "Microbubble Size Isolation by Differential Centrifugation," Journal of Colloid and Interface Science, 329, pp. 316-324 (2009).
Forsberg et al., "Subharmonic imaging of contrast agents," Ultrasonics, vol. 38, pp. 93-98 (2000).
Ganan-Calvo et al., "Perfectly Monodisperse Microbubbling by Capillary Flow Focusing," Physical Review Letters, vol. 87, No. 27, pp. 274501-1-274501-4 (2001).
Gao et al., "Drug-Loaged Nano/Microbubbles for Combining Ultrasonography and Targeted Chemotherapy," Ultrasonics, vol. 48, No. 4, pp. 1-24 (Aug. 2008).
Garstecki et al., "Formation of Bubbles and Droplets in Microfluidic Systems," Bulletin of the Polish Academy of Sciences, vol. 53, No. 4, pp. 361-372 (2005).
Gessner et al., "High-Resolution, High-Contrast Ultrasound Imaging Using a Prototype Dual-Frequency Transducer: In Vitro and In Vivo Studies," IEEE Transactions on Ultrasonics, Ferroelectrics, and Frequency Control, vol. 57, No. 8, pp. 1772-1781 (Aug. 2010).
Gessner et al., "Advances in Molecular Imaging with Ultrasound," Mol Imaging, vol. 9, No. 3, pp. 1-21 (Jun. 2010).
Gessner et al., "Radiation Force-Enhanced Targeted Imaging and Near Real-time Molecular Imaging Using a Dual-Frequency High-Resolution Transducer: In-vitro and In-vivo Results," Proceedings of the 2009 IEEE Ultrasonics Symposium, In Press, pp. 1-4, (2009).
Gessner et al., "Radiation Force-Enhanced Targeted Imaging Using a Dual-Frequency High Resolution Transducer," Abstract Submitted for Peer Review (Publication Date Unknown).
Gessner et al., "High-Resolution In-Vivo Ultraharmonic Contrast Imaging using a Dual-Frequency Transducer," Abstract Submitter for Peer Review (Publication Date Unknown).
Giesecke et al., "Ultrasound-Mediate Cavitation Thresholds of Liquid Perfluorocarbon Droplets in Vitro," Ultrasound in Medicine & Biology, vol. 29, No. 9, pp. 1359-1365 (2003).
Gingrich et al., "Partial CviJI Digestion as an Alternative Approach to Generate Cosmid Sublibraries for Large-Scale Sequencing Projects," Biotechniques, vol. 21 (1), pp. 99-104 (1996).
Giresi et al., "Isolation of Active Regulatory Elements from Eukaryotic Chromatin Using FAIRE (Formaldehyde Assisted Isolation of Regulatory Elements)," Methods, vol. 48, No. 3, pp. 1-13 (Jul. 2009).
Goll, "Design of Broad-Band Fluid-Loaded Ultrasonic Transducers," IEEE Transactions on Sonics and Ultrasonics, vol. SU-26, No. 6, pp. 385-393 (Nov. 1979).

(56) References Cited

OTHER PUBLICATIONS

Gramiak et al., "Echocardiography of the aortic root," Invest. Radiol., vol. 3, pp. 356-366 (1968).
Groschl, "Ultrasonic Separation of Suspending Particles—Part I: Fundamentals," Acustica, vol. 84, pp. 432-447 (1998).
Haworth et al., "Towards Aberration Correction of Transcranial Ultrasound Using Acoustic Droplet Vaporization," Ultrasound Med Biol, vol. 34, No. 3, pp. 1-24 (Mar. 2008).
Hengen, "Shearing DNA for Genomic Library Construction," Trends in Biochemical Sciences, vol. 22, pp. 273-274 (1997).
Hettiarachchi et al., "Controllable Microfluidic Synthesis of Multiphase Drug-Carrying Lipospheres for Site-Targeted Therapy," Biotechnology Progress, vol. 25, No. 4, pp. 1-17 (2009).
Hettiarachchi et al., "On-chip Generation of Microbubbles as a Practical Technology for Manufacturing Contrast Agents for Ultrasonic Imaging," Lab Chip., vol. 7, No. 4, pp. 1-14 (Apr. 2007).
Hitchcock et al., "Ultrasound-Assisted Thrombolysis for Stroke Therapy: Better Thrombus Break-up with Bubbles," Stroke, vol. 41, pp. 1-8 (Oct. 2010).
Hobbs et al., "Regulation of Transport Pathways in Tumor Vessels: Role of Tumor Type and Microenvironment," Proceedings of the National Academy of Sciences, vol. 95, No. 8, pp. 4607-4612 (Apr. 1998).
Hoff et al., "Oscillations of Polymeric Microbubbles: Effect of the Encapsulating Shell," The Journal of the Acoustical Society of America, vol. 107, No. 4, pp. 2272-2280 (2000).
Hoffman et al., "Genome-Wide Identification of DNA-Protein Interactions Using Chromatin Immunoprecipitation Coupled with Flow Cell Sequencing," Journal of Endocrinology, vol. 201(1), pp. 1-13 (2009).
Hoheisel et al., "Control of Partial Digestion Combining the Enzymes dam Methylase and MboI," Nucleic Acids Research, vol. 17, No. 23, pp. 9571-9582 (1989).
Hopp et al., "Factory Physics, Foundations of Manufacturing Management," Second Edition, Chapter 7, pp. 213-227 (2008).
Huh et al., "A Gravity-Driven Microfluidic Particle Sorting Device with Hydrodynamic Separation Amplification," Analytical Chemistry, vol. 79, pp. 1-14 (Feb. 2007).
Hurrell, "Voltage to pressure conversion: are you getting 'phased' by the problem?," Journal of Physics: Conference Series, vol. 1, p. 57 (2004).
Hynynen et al., "Local and Reversible Blood-Brain Barrier Disruption by Noninvasive Focused Ultrasound at Frequencies Suitable for Trans-skull Sonications," NeuroImage, vol. 24, pp. 12-20 (2005).
Iyer et al., "Exploiting the Enhanced Permeability and Retention Effect for Tumor Targeting," Drug Discovery Today, vol. 11, No. 17/18, pp. 812-818 (2006).
Janzen et al., "Epigenetics: Tools and Techologies," Drug Discov Today Technol., vol. 7, No. 1, pp. 1-13 (2010).
Janzen et al., "High Throughput Screening. Methods and Protocols, Second Edition," (2009).
Janzen et al., "Review: Advances in Improving the Quality and Flexibility of Compound Management," Journal of Biomolecular Screening, vol. 14, No. 5, pp. 444-451 (2009).
Janzen, "High Throughput Screening: Methods and Protocols," (2002).
Jayaweera et al., "In Vivo Myocardial Kinetics of Air-Filled Albumin Microbubbles During Myocardial Contrast Echocardiography. Comparison with Radiolabeled Red Blood Cells," Circulation Research—The Journal of the American Heart Association, vol. 74, No. 6, pp. 1157-1165 (1994).
Jones et al., "Prospective Thermal Dosimetry: The Key to Hyperthermia's Future," International Journal of Hyperthermia, vol. 22, No. 3, pp. 247-253 (May 2006).
Ten Kate et al., "Molecular imaging of inflammation and intraplaque vasa vasorum: a step forward to identification of vulnerable plaques?," J. Nucl. Cardiol., vol. 17, pp. 897-912 (2010).
Kawabata et al., "Nanoparticles with Multiple Perfluorocarbons for Controllable Ultrasonically Induced Phase Shifting," Japanese Journal of Applied Physics, vol. 44, No. 6B, pp. 4548-4552.

Kaya et al., "Acoustic Responses of Monodisperse Lipid Encapsulated Microbubble Contrast Agents Produced by Flow Focusing," Bubble Science, Engineering and Technology, vol. 2, No. 2, pp. 33-40 (Dec. 2010).
Kaya et al., "Changes in Lipid-Encapsulated Microbubble Population During Continuous Infusion and Methods to Maintain Consistency," Ultrasound in Medicine & Biology, vol. 35, No. 10, pp. 1-16 (Oct. 2009).
King et al., "Comparison between maximum radial expansion of ultrasound contrast agents and experimental postexcitation signal results," J. Acoust. Soc. Am., vol. 129, pp. 114-121 (2011).
King et al., "Determination of postexcitation thresholds for single ultrasound contrast agent microbubbles using double passive cavitation detection," J. Acoust. Soc. Am., vol. 127, pp. 3449-3455 (2010).
Klibanov, "Microbubble Contrast Agents—Targeted Ultrasound Imaging and Ultrasound-Assisted Drug-Delivery Applications," Investigative Radiology, vol. 41, No. 3, pp. 354-362 (2006).
Klibanov et al., "Targeting and Ultrasound Imaging of Microbubble-based Contrast Agents," Magnetic Resonance Materials in Physics, Biology, and Medicine, vol. 8, pp. 177-184 (1999).
Klibanov et al., "Targeting of Ultrasound Contrast Material. An in vitro Feasibility Study," Acta Radiologica, Supplement 412, pp. 113-120 (1997).
Knierim et al., "Systematic Comparison of Three Methods for Fragmentation of Long-range PCR Products for Next Generation Sequencing," PLoS ONE, vol. 6, Issue 11, e28240, pp. 1-6 (Nov. 2011).
Kripfgans et al., "Acoustic Droplet Vaporization for Temporal and Spatial Control of Tissue Occlusion: A Kidney Study," IEEE Transactions on Ultrasonics, Ferroelectrics, and Frequency Control, vol. 52, No. 7, pp. 1101-1110 (2005).
Kripfgans et al., "On the Acoustic Vaporization of Micrometer-Sized Droplets," The Journal of the Acoustical Society of America, vol. 116, No. 1, pp. 272-281 (2004).
Kripfgans et al., "In Vivo Droplet Vaporization for Occlusion Therapy and Phase Aberration Correction," IEEE Transactions on Ultrasonics, Ferroelectrics, and Frequency Control, vol. 49, pp. 726-738 (2002).
Kripfgans et al., "Acoustic Droplet Vaporization for Therapeutic and Diagnostic Applications," Ultrasound in Med. & Biol., vol. 26, No. 7, pp. 1177-1189 (2000).
Krishnan et al., "Inertial lift on a Moving Sphere in Contact with a Plane Wall in a Shear Flow," Phys. Fluids, vol. 7, No. 11, pp. 2538-2545 (1995).
Kruse et al., "Spatial and Temporal-Controlled Tissue Heating on a Modified Clinical Ultrasound Scanner for Generating Mild Hyperthermia in Tumors," IEEE Transactions on Biomedical Engineering, vol. 57, No. 1, pp. 155-166 (Jan. 2010).
Kruse et al., "A New Imaging Strategy Using Wideband Transient Response of Ultrasound Contrast Agents," IEEE Transactions on Ultrasonics, Ferroelectrics and Frequency Control, vol. 52, No. 8, pp. 1-22 (Aug. 2005).
Kwan et al., "Microbubble Dissolution in a Multigas Environment," Langmuir, vol. 26, No. 9,, pp. 6542-6548 (2010).
Lamberti et al., "A New Approach for the Design of Ultrasono-Therapy Transducers," IEEE Transactions on Ultrasonics, Ferroelectrics, and Frequency Control, vol. 44, No. 1, pp. 77-84 (Jan. 1997).
Landmark et al., "Pharmacokinetics of Perfluorobutane Following Intravenous Bolus Injection and Continuous Infusion of Sonazoid™ in Healthy Volunteers and in Patients with Reduced Pulmonary Diffusing Capacity," Ultrasound in Med. & Biol., vol. 34, No. 3, pp. 494-501 (2008).
"DEFINITY®," Lantheus Medical Imaging. WayBack Machine https://web.archive.org/web/20101123011336/http://www.definityimaging.com/main.html? (Nov. 23, 2010).
Lanza et al., "Targeted Ultrasonic Contrast Agents for Molecular Imaging and Therapy," Current Problems in Cardiology, pp. 625-653 (Dec. 2003).
Lanza et al., "High-Frequency Ultrasonic Detection of Thrombi with a Targeted Contrast System," Ultrasound in Med. & Biol., vol. 23, No. 6, pp. 863-870 (1997).

(56) References Cited

OTHER PUBLICATIONS

Lanza et al., "A Novel Site-Targeted Ultrasonic Contrast Agent with BRoad Biomedical Application,," Circulation, vol. 94, pp. 1-9 (1996).
Lediju et al., "Short-lag spatial coherence imaging," 2010 IEEE International Ultrasonics Symposium, pp. 987-990 (2010).
Lee et al., "Oscillatory Vaporization and Acoustic Response of Droplet at High Pressure," International Communications in Heat and Mass Transfer, vol. 35, No. 10, pp. 1302-1306 (2008).
Leong-Poi eet al., "Noninvasive Assessment of Angiogenesis by Ultrasound and Microbubbles Targeted to αv-Integrins," Circulation—Journal of the American Heart Association, vol. 107, pp. 455-460 (2003).
Lindner, "Contrast Ultrasound Molecular Imaging of Inflammation in Cardiovascular Disease," Cardiovascular Research, vol. 84, pp. 182-189 (2009).
Lindner, "Microbubbles in Medical Imaging: Current Applications and Future Directions," Nature Reviews—Drug Discovery, vol. 3, pp. 527-532 (Jun. 2004).
Lindner, "Evolving Applications for Contrast Ultrasound," The American Journal of Cardiology, vol. 90, No. 10A, pp. 72J-80J (2002).
Lindner et al., "Delivery Drugs with Ultrasound," Echocardiography, vol. 18, No. 4, pp. 329-337 (May 2001).
Lindner et al., "Assessment of Resting Perfusion with Myocardial Contrast Echocardiography: Theoretical and Practical Considerations," The American Heart Journal, vol. 139, No. 2, Part 1, pp. 231-240 (2000).
Lindner et al., "Noninvasive Ultrasound Imaging of Inflammation Using Microbubbles Targeted to Activated Leukocytes," Circulation—Journal of the American Heart Association, vol. 102, No. 22, pp. 2745-2750 (2000).
Linker et al., "In Vivo Molecular Imaging of Adhesion Molecules in Experimental Autoimmune Encephalomyelitis (EAE)," Journal of Autoimmunity, vol. 25, pp. 199-205 (2005).
Lo et al., "Acoustic Droplet Vaporization Threshold: Effects of Pulse Duration and Contrast Agent," IEEE Transactions on Ultrasonics, Ferroelectrics, and Frequency Control, vol. 54, No. 5, pp. 933-946 (2007).
Lo et al., "Spatial Control of Gas Bubbles and Their Effects on Acoustic Fields," Ultrasound Med Biol., vol. 32, No. 1, pp. 95-106 (2006).
Lockwood et al., "Modeling and Optimization of High-Frequency Ultrasound Transducers," IEEE Transactions on Ultrasonics, Ferroelectrics, and Frequency Control, vol. 41, No. 2, pp. 225-230 (Mar. 1994).
Lum et al., "Ultrasound Radiation Force Enables Targeted Deposition of Model Drug Carriers Loaded on Microbubbles," Journal of Controlled Release, vol. 111, No. 1-2, pp. 1-15 (Mar. 2006).
Macedo et al., "Acoustic Effects on Gas Bubbles in the Flows of Viscous Fluids and Whole Blood," The Journal of the Acoustical Society of America, vol. 53, No. 5, pp. 1327-1335 (1973).
Marmottant et al., "A Model for Large Amplitudee Oscillations of Coated Bubbles Accounting for Buckling and Rupture," The Journal of the Acoustical Society of America, vol. 118, No. 6, pp. 3499-3505 (2005).
Marsh et al., "Molecular Imaging with Targeted Perfluorocarbon Nanoparticles: Quantification of the Concentration Dependence of Contrast Enhancement for Binding to Sparse Cellular Epitopes," Ultrasound Med Biol., vol. 33, No. 6, pp. 1-16 (Jun. 2007).
Martin et al., "Current status and prospects for microbubbles in ultrasound theranostics," Wiley Interdisciplinary Reviews: Nanomedicine and Nanobiotechnology, vol. 5, pp. 329-345 (2013).
Martz et al., "Precision Manufacture of Phase-Change Perfluorocarbon Droplets Using Microfluidics," Ultrasound Med Biol., vol. 37, No. 11, pp. 1-13 (Nov. 2011).
Matsuura et al., "Nanoparticle-Loaded Perfluorocarbon Droplets for Imaging and Therapy," IEEE International Ultrasonics Symposium (IUS), pp. 5-8 (2009).
Mattrey, "The Potential Role of Perfluorochemicals (PFCS) in Diagnostic Imaging," Artifical Cells, Blood Substitutes, and Immobilization Biotechnology, vol. 22, No. 2, pp. 295-313 (1994).
McKeighen, "Design Guidelines for Medical Ultrasonic Arrays," SPIE, vol. 3341, pp. 1-18 (1998).
Meairs et al., "Microbubbles for Thrombolysis of Acute Ischemic Stroke," Cerebrovascular Diseases, vol. 27, pp. 55-65 (Apr. 16, 2009).
Meyer et al., "Freestream Nuclei and Traveling-Bubble Cavitation," Transactions of the ASME, vol. 114, pp. 672-679 (Dec. 1992).
Meyerson et al., "Advances in Understanding Cancer Genomes Through Second-Generation Sequencing," Nature Reviews, Genetics, vol. 11, pp. 685-696 (Oct. 2010).
Miller et al., "Bioeffects Considerations for Diagnostic Ultrasound Contrast Agents," J Ultrasound Med, vol. 27, pp. 611-632 (2008).
Miller et al., "Lysis and Sonoporation of Epidermoid and Phagocytic Monolayer Cells by Diagnostic Ultrasound Activation of Contrast Agent Gas Bodies," Ultrasound in Medicine and Biology, vol. 27, No. 8, pp. 1107-1113 (2001).
Miller et al., "Sonoporation of Monolayer Cells by Diagnostic Ultrasound Activation of Contrast-Agent Gas Bodies," Ultrasound in Medicine and Biology, vol. 26 No. 4, pp. 661-667 (2000).
Miller et al., "Cavitation Nucleation Agents for Nonthermal Ultrasound Therapy," Journal of the Acoustical Society of America, vol. 107, No. 6, pp. 3480-3486 (Jun. 2000).
Miller et al., "Sonoporation of Cultured Cells in the Rotating Tube Exposure System," Ultrasound in Medicine and Biology, vol. 25, No. 1, pp. 143-449 (1999).
Minnaert, "On musical air-bubbles and the sounds of running water," Philosophical Magazine, vol. 16, pp. 235-248 (1933).
Misaridis et al., "Use of modulated excitation signals in medical ultrasound. Part 1: Basic concepts and expected benefits," IEEE Transactions on Ultrasonics Ferroelectrics and Frequency Control, vol. 52, pp. 177-191 (2005).
Mitragotri, "Healing Sound: The Use of Ultrasound in Drug Delivery and Other Therapeutic Applications," Nature Revies, Drug Discovery, vol. 4, pp. 255-260 (Mar. 2005).
Morgan, "Experimental and Theoretical Evaluation of Ultrasonic Contrast Agent Behavior," Dissertation, University of Virginia, (Jan. 2001).
Morgan et al., "Experimental and Theoretical Evaluation of Microbubble Behavior: Effect of Transmitted Phase and Bubble Size," IEEE Transactions on Ultrasonics, Ferroelectrics, and Frequency Control, vol. 47, No. 6, pp. 1494-1509 (Nov. 2000).
Morgan et al., "Experimental and Theoretical Analysis of Individual Contrast Agent Behavior," IEEE Ultrasonics Symposium, vol. 2, pp. 1685-1688 (1999).
Morgan et al., "Changes in the Echoes from Ultrasonic Contrast Agents with Imaging Parameters," IEEE Transactions on Ultrasonics, Ferroelectrics, and Frequency Control, vol. 45, No. 6, pp. 1537-1548 (Nov. 1998).
Mulvagh et al., "Contrast Echocardiography: Current and Future Applications," Journal of the American Society of Echocardiography, vol. 13, No. 4, pp. 331-342 (Apr. 2000).
Needles et al., "Nonlinear contrast imaging with an array-based micro-ultrasound system," Ultrasound in Medicine & Biology, vol. 36, pp. 2097-2106 (2010).
Nyborg, "Solutions of the Bio-Heat Transfer Equation," Physics in Medicine and Biology, vol. 33, No. 7, pp. 785-792 (1988).
Oakley, "Calculation of Ultrasonic Transducer Signal-to-Noise Rations Using the KLM Model," IEEE Transactions on Ultrasonics, Ferroelectrics, and Frequency Control, vol. 44, No. 5, pp. 1018-1026 (Sep. 1997).
Oefner et al., "Efficient Random Subcloning of DNA Sheared in Recirculating Point-Sink Flow System," Nucleic Acids Research, vol. 24, No. 20, pp. 3879-3886 (1996).
Okpodu et al., "Rapid Isolation of Nuclei From Carrot Suspension Culture Cells Using a BioNebulizer," BioTechniques, vol. 16, No. 1, pp. 154-158 (1994).
Osoegawa et al., "A Bacterial Artifical Chromosome Library for Sequencing the Complete Human Genome," Genome Research, vol. 11, No. 3, pp. 483-496 (2001).

(56) References Cited

OTHER PUBLICATIONS

Pan et al., "Study of Sonoporation Dynamics Affected by Ultrasound Duty Cycle," Ultrasound in Medicine and Biology, vol. 31, No. 6, pp. 849-856 (2005).
Pan et al., "Sonoporation of Cells for Drug and Gene Delivery," Conf Proc IEEE Eng Med Biol Soc, vol. 5 pp. 3531-3534 (2004).
Pancholi et al., "Novel Methods for Preparing Phospholipid Coated Microbubbles," Eur. Blophys. J., vol. 37, pp. 515-520 (2008).
Pancholi et al., "Generation of Microbubbles for Diagnostic and Therapeutic Applications Using a Novel Device," Journal of Drug Targeting, vol. 16, No. 6, pp. 494-501 (Jul. 2008).
Park et al., "Unsteady Forces on Spherical Bubbles," Experiments in Fluids, vol. 19, pp. 167-172 (1995).
Patil et al., "Particle Diameter Influences Adhesion Under Flow," Biophysical Journal, vol. 80, pp. 1733-1743 (Apr. 2001).
Pitt et al., "Phase Transitions of Perfluorocarbon Nanoemulsion Induced with Ultrasound: A Mathematical Model," Ultrasonics Sonochemistry, vol. 21, pp. 879-891 (2014).
Pitt et al., "Ultrasonic Drug Delivery—A General Review," Expert Opinion on Drug Delivery, vol. 1, pp. 1-32 (Nov. 2004).
Plesset et al., "Bubble Dynamics and Cavitation," Annu. Rev. Fluid Mech., vol. 9, pp. 145-185 (1977).
Popa-Burke et al., "Streamlined System for Purifying and Quantifying a Diverse Library of Compounds and the Effect of Compound Concentration Measurements on the Accurate Interpretation of Biological Assay Results," Analytical Chemistry, vol. 76, No. 24, pp. 7278-7287 (Dec. 15, 2004).
Price et al., "Delivery of Colloidal Particles and Red Blood Cells to Tissue Through Microvessel Ruptures Created by Targeted Microbubble Destruction with Ultrasound," Journal of the American Heart Association, vol. 98, pp. 1264-1267 (Sep. 29, 1998).
Prosperetti, "Bubble Phenomena in Sound Fields: Part Two," Ultrasonics, vol. 22, pp. 115-124 (May 1984).
Qamar et al., "Dynamics of Acoustic Droplet Vaporization in Gas Embolotherapy," Applied Physics Letters, vol. 96, pp. 143702-1-143702-3 (2010).
Qamar et al., "Evolution of acoustically vaporized microdroplets in gas embolotherapy," Journal of Biomechanical Engineering, vol. 134, pp. 031010-1-031010-13 (2012).
Rapoport, "Phase-shift, stimuli-responsive perfluorocarbon nanodroplets for drug delivery to cancer," Wiley Interdisciplinary Reivews: Nanomedicine and Nanobiotechnology, vol. 4, pp. 492-510 (2012).
Rapoport et al., "Ultrasound-mediated tumor imaging and nanotherapy using drug loaded, block copolymer stabilized perfluorocarbon nanoemulsions," Journal of Controlled Release, vol. 153, pp. 4-15 (2011).
Rapoport et al., "Cavitation Properties of Block Copolymer Stabilized Phase-Shift Nanoemulsions Used as Drug Carriers," Ultrasound Med Biol, vol. 36, No. 3, pp. 1-21 (Mar. 2010).
Rapoport et al., "Controlled and Targeted Tumor Chemotherapy by Ultrasound-activated Nanoemulsions/Microbubbles," J Control Release, vol. 138, No. 3, pp. 1-25 (Sep. 15, 2009).
Rapoport et al., "Microbubble Generation in Phase-Shift Nanoemulsions Used as Anticancer Drug Carriers," Bubble Sci Eng Technol, vol. 1, pp. 1-21 (2009).
Rapoport et al., "Multifunctional Nanoparticles for Combining Ultrasonic Tumor Imaging and Targeted Chemotherapy," J Natl Cancer Inst, vol. 99, pp. 1095-1106 (2007).
Reddy et al., "Coupled Dynamics of Translation and Collapse of Acoustically Driven Microbubbles," J. Acoust. Soc. Am., vol. 112, No. 4, pp. 1346-1352 (Oct. 2002).
Reinhardt et al., "Ultrasound Derived Imaging and Quantification of Cell Adhesion Molecules in Experimental Autoimmune Encephalomyelitis (EAE) by Sensitive Particle Acoustic Quantification (SPAQ)," NeuroImage, vol. 27, pp. 267-278 (2005).
Reznik et al., "The efficiency and stability of bubble formation by acoustic vaporization of submicron perfluorocarbon droplets," Ultrasonics, vol. 53, pp. 1368-1376 (2013).
Reznik et al., "Investigation of Vaporized Submicron Perfluorocarbon Droplets as an Ultrasound Contrast Agent," Ultrasound in Medicine & Biology, vol. 37, pp. 1271-1279 (2011).
Roe, "Shotgun Library Construction for DNA Sequencing," Methods in Molecular Biology, vol. 255, pp. 171-187 (2004).
Rychak et al., "Enhanced Targeting of Ultrasound Contrast Agents Using Acoustic Radiation Force," Ultrasound in Medicine and Biology, vol. 33, No. 7, pp. 1132-1139 (Jul. 2007).
Rychak et al., "Acoustic Radiation Force Enhances Targeted Delivery of Ultrasound Contrast Microbubbles: In Vitro Verification," IEEE Transactions on Ultrasonics, Ferroelectrices, and Frequency Control, vol. 52, No. 3, pp. 421-433 (Mar. 2005).
Rychak et al., "Deformable Gas-Filled Microbubbles Targeted to P-Selectin," Journal of Controlled Release, vol. 114, pp. 288-299 (2006).
Salgaonkar et al., "Passive cavitation imaging with ultrasound arrays," The Journal of the Acoustical Society of America, vol. 126, pp. 3071-3083 (2009).
Sassaroli et al., "Cavitation threshold of microbubbles in gel tunnels by focused ultrasound," Ultrasound in Medicine Biology, vol. 33, pp. 1651-1660 (2007).
Sboros et al., "The Assessment of Microvascular Flow and Tissue Perfusion Using Ultrasound Imaging," Proceedings of the Institution of Mechanical Engineers, Part H: Journal of Engineerying in Medicine, vol. 224, pp. 273-290 (2010).
Sboros, "Response of Contrast Agents to Ultrasound," Advanced Drug Delivery Reviews, No. 60, pp. 1117-1136 (Mar. 2008).
Schad et al., "In Vitro Characterization of Perfluorocarbon Droplets for Focused Ultrasound Therapy," Physics in Medicine and Biology, vol. 55, pp. 4933-4947 (2010).
Schoppee et al., "Chromatin Immunoprecipitation (ChiP): Revisiting the Efficacy of Sample Preparation, Sonication, Quantification of Sheared DNA, and Analysis via PCR," PLoS ONE, vol. 6, Issue 10, e26015, pp. 1-10 (Oct. 2011).
Schroeder et al., "Ultrasound Triggered Release of Cisplatin from Liposomes in Murine Tumors," Journal of Controlled Release, vol. 137, pp. 63-68 (2009).
Schumann et al., "Targeted-Microbubble Binding Selectively to GPIIB IIIa Receptors of Platelet Thrombi," Investigative Radiology, vol. 37, No. 11, pp. 587-593 (Nov. 2002).
Seed et al., "Representation of DNA Sequences in Recombinant DNA Libraries Prepared by Restriction Enzyme Partial Digestion," Gene, vol. 19, pp. 201-209 (Jun. 1982).
Selfridge et al., "KLM Transducer Model Implementation Using Transfer Matrices," IEEE Ultrasonics Symposium, pp. 875-877 (1985).
Sheeran et al., "Vaporization phenomena for ultrasound phase-change contrast agents assessed via high-speed optical microscopy," 2013 IEEE International Ultrasonics Symposium (IUS), pp. 1841-1844 (Jul. 21-25, 2013).
Sheeran et al., "Toward ultrasound molecular imaging with phase-change contrast agents: an in vitro proof of principle," Ultrasound Med. Biol., vol. 39, No. 5, pp. 893-902 (May 2013).
Sheeran et al., "Phase-transition thresholds and vaporization phenomena for ultrasound phase-change nanoemulsions assessed via high-speed optical microscopy," Physics in Medicine and Biology, vol. 58, p. 4513 (2013).
Sheeran et al., "Phase-change contrast agents for imaging and therapy," Curr. Pharm. Des., vol. 18, pp. 2152-2165 (2012).
Sheeran et al., "Design of Ultrasonically-Activatable Nanoparticles using Low Boiling Point Perfluorocarbons," Biomaterials, vol. 33, No. 11, pp. 1-21 (Apr. 2012).
Sheeran et al., "Decafluorobutane as a Phase-Change Contrast Agent for Low-Energy Extravascular Ultrasonic Imaging," Ultrasound in Medicine and Biology, vol. 37, No. 9, pp. 1518-1530 (2011).
Sheeran et al., "Perfluorobutane as a Phase-Change Contrast Agent for Low-Energy Extravascular Ultrasound Imaging," pp. 1-8 (Publication Date Unknown).
Shortencarier et al., "A Method for Radiation-Force Localized Drug Delivery Using Gas-Filled Liposheres", IEEE Transactions on Ultrasonics, Ferroelectrics and Frequency Control, vol. 51, No. 7, pp. 822-831 (Jul. 2004).

(56) References Cited

OTHER PUBLICATIONS

Shpak et al., "Ultrafast dynamics of the acoustic vaporization of phase-change microdroplets," Journal of the Acoustical Society of America, vol. 134, pp. 1610-1621 (2013a).
Shpak et al., "The role of gas in ultrasonically driven bapor bubble growth," Physics in Medicine and Biology, vol. 58, pp. 2523-2535 (2013b).
Sirsi et al., "Microbubble Compositions, Properties and Biomedial Applications," Bubble Sci. Eng. Technol., vol. 1, pp. 1-28 (Nov. 2009).
Sittampalam et al., "Design of Signal Windows in High Throughput Screening Assays for Drug Discovery," Journal of Biomolecular Screening, vol. 2, No. 3, pp. 159-169 (1997).
Sittampalam et al., "High-Throughput Screening: Advances in Assay Technologies," Current Opinion in Chemical Biology, vol. 1(3), pp. 384-391 (1997).
Staub et al., "Contrast-Enhanced Ultrasound Imaging of the Vasa Vasorum: From Early Atherosclerosis to the Identification of Unstable Plaques," J. Am. Coll. Cardiol. Img., vol. 3, No. 7, pp. 761-771 (Jul. 2010).
Stephens et al., "Efficient Array Design for Sonotherapy," Phys Med Biol., vol. 53, No. 14, pp. 1-42 (Jul. 21, 2008).
Stephens et al., "Multi-frequency Array Development for Drug Delivery Therapies: Characterization and First Use of a Triple Row Ultrasound Probe," IEEE Ultrasonics Symposium, pp. 66-69 (2006).
Stieger et al., "Imaging of Angiogenesis Using Cadence Contrast Pulse Sequencing and Targeted Contrast Agents," Contrast Media & Molecular Imaging, vol. 3(1), pp. 9-18 (2008).
Stieger et al., "Enhancement of Vasular Permeability with Low-Frequency Contrast-Enhanced Ultrasound in the Chorioallantoic Membrane Model," Radiology, vol. 243, No. 1, pp. 112-121 (Apr. 2007).
Streeter et al., "Improving Sensitivity in Ultrasound Molecular Imaging by Tailoring Contrast Agent Size Distribution: In Vivo Studies," Molecular Imaging, vol. 9, No. 2, pp. 1-18 (Apr. 2010).
Stride et al., "Cavitation and Contrast: The Use of Bubbles in Ultrasound Imaging and Therapy," Proceedings of the Institution of Mechanical Engineers, Part H: Journal of Engineering in Medicine, vol. 224, pp. 171-191 (2010).
Strohm et al., "Vaporization of perfluorocarbon droplets using optical irradiation," Biomed. Opt. Express, vol. 2, pp. 1432-1442 (2011).
Takeuchi et al., "Enhanced Visualization of Intravascular and Left Atrial Appendage Thrombus with the Use of a Thrombus-Targeting Ultrasonographic Contrast Agent (MRX-408A1): In Vivo Experimental Echocardioraphic Studies," Journal of the American Society of Echocardiography, vol. 12, No. 12, pp. 1015-1021 (Dec. 1999).
Talu et al., "Needle Size and Injection Rate Impact Microbubble Contrast Agent Population," Ultrasound in Medicine & Biology, vol. 34, No. 7, pp. 1-8 (Jul. 2008).
Talu et al., "Maintaining Monodispersity in a Microbubble Population Formed by Flow-Focusing," Langmuir, vol. 24, No. 5, pp. 1-14 (Mar. 2008).
Talu et al., "Tailoring the Size Distribution of Ultrasound Contrast Agents: Possible Method for Improving Sensitivity in Molecular Imaging," Molecular Imaging, vol. 6, No. 6, pp. 1-19 (2007).
Talu et al., "Long-Term Stability by Lipid Coating Monodisperse Microbubbles Formed by a Flow-Focusing Device," Langmuir, vol. 22, No. 23, pp. 1-10 (Nov. 7, 2006).
Tan et al., "Microfluidic Separation of Satellite Droplets as the Basis of a Monodispersed Micron and Submicron Emulsification System," Lab Chip, vol. 5, pp. 1178-1183 (2005).
Tan et al., "Design of Microfluidic Channel Geometries for the Control of Droplet Volume, Chemical Concentration, and Sorting," Lab Chip, vol. 4, pp. 292-298 (2004).
Tartis et al., "Therapeutic Effects of Paclitaxel-Containing Ultrasound Contrast Agents," Ultrasound in Medicine and Biology, vol. 32, No. 11, pp. 1771-1780 (2006).
Teh et al., "Droplet Microfluidics," Lab Chip, vol. 8, pp. 198-220 (2008).

Ten Kate et al., "Molecular Imaging of Inflammation and Intraplaque Vasa Vasorum: A Step Forward to Identification of Vulnerable Plaques?," Journal of Nuclear Cardiology, vol. 17, pp. 897-912 (2010).
Teytelman et al., "Impact of Chromatin Structures on DNA Processing for Genomic Analyses," PLoS ONE, vol. 4, Issue 8, e6700, pp. 1-11 (Aug. 2009).
Thorstenson et al., "An Automated Hydrodynamic Process for Controlled, Unbiased DNA Shearing," Genome Research, vol. 8, pp. 848-855 (Aug. 1998).
Tinkov et al., "Microbubbles as Ultrasound Triggered Drug Carriers," Journal of Pharmaceutical Sciences, vol. 98, No. 6, pp. 1935-1961 (2009).
Torchilin, "Passive and Active Drug Targeting: Drug Delivery to Tumors as an Example," Handbook of Experimental Pharmacology, pp. 3-53 (2010).
Tortoli et al., "Unexpected Doppler Effects from Microbubbles Moving Through an Ultrasound Beam," IEEE Ultrasonics Symposium, vol. 2, pp. 1729-1732 (1999).
Ueda et al., "Acoustic Cavitation as an Enhancing Mechanism of Low-Frequency Sonophoresis for Transdermal Drug Delivery," Biol. Pharm. Bull, vol. 32, No. 5, pp. 916-920 (2009).
Unger et al., "Therapeutic Applications of Lipid-Coated Microbubbles," Advanced Drug Delivery Reviews, vol. 56, pp. 1291-1314 (2004).
Unger et al., "Therapeutic Applications of Microbubbles," European Journal of Radiology, vol. 42, pp. 160-688 (2002).
Unger et al., "Local Drug and Gene Delivery Through Microbubbles," Progress in Cardiovascular Diseases, vol. 44, No. 1, pp. 45-54 (Jul./Aug. 2001).
Unger et al., "In Vitro Studies of a New Thrombus-Specific Ultrasound Contrast Agent," Am J Cardiol, vol. 81, No. 12A, pp. 58G-61G (1998).
Van Wamel et al., "Vibrating Microbubbles Poking Individual Cells: Drug Transfer Into Cells Via Sonoporation," Journal of Controlled Release, vol. 112, pp. 149-155 (2006).
Villanueva, "Molecular Imaging of Cardiovascular Disease Using Ultrasound," J. Nucl. Cardiol., vol. 15, No. 4, pp. 1-18 (2008).
Villanueva et al., "Microbubbles Targeted to Intracellular Adhesion Molecule-1 Bind to Activated Coronary Artery Endothelial Cells," Circulation, vol. 98, pp. 1-6 (1998).
Vorkurka, "Comparison of Rayleigh's, Herring's, and Gilmore Models of Gas Bubbles," Acustica, vol. 59, pp. 214-219 (1986).
Walters et al., "Prediction of 'drug-likeness'", Advanced Drug Delivery Reviews, vol. 54, pp. 255-271 (2002).
Wang et al., "Controllable Microfluidic Production of Multicomponent Multiple Emulsions," Lab Chip, vol. 11, pp. 1587-1592 (Mar. 9, 2011).
Ward et al., "Experimental Study of the Effects of Optison Concentration on Sonoporation In Vitro," Ultrasound in Medicine & Biology, vol. 26, No. 7, pp. 1169-1175 (May 2, 2000).
Watanabe et al., "Translational and Radical Motions of a Bubble in an Acoustic Standing Wave Field," Phys. Fluids A, vol. 5, No. 11, pp. 2682-2688 (Nov. 1993).
Wei et al., "Recent Advances in Myocardial Contrast Echoardiography," Curr. Opin. Cardiol., vol. 12, pp. 539-546 (1997).
Whittingham, "Contrast-specific imaging techniques: technical perspective," Contrast Media in Ultrasonography: Basic Principles and Clinical Applications, pp. 43-70 (2005).
Whitworth, "Discussion of One-D Piezoelectric Transducer Models With Loss," IEEE Transactions on Ultrasonics, Ferroelectrics and Frequency Control, vol. 48, No. 3, pp. 844-846 (May 2001).
Wigle et al., "Accessing Protein Methyltransferase and Dementhylase Enzymology Using Microfluidic Capillary Electrophoresis," Chem Biol., vol. 17, No. 7, pp. 1-19 (2010).
Wigle et al., "Screening for Inhibitors of Low-Affinity Epigenetic Peptide-Protein Interactions: An AlphaScreen™-Based Assay for Antagonists of Methyl-Lysine Binding Proteins," Journal of Biomolecular Screening, vol. 15, No. 1, pp. 62-71 (2010).
Wilson et al., "Biomedical photoacoustics beyond thermal expansion using triggered nanodroplet vaporization for contrast-enhanced imaging," Nature Communications, vol. 3, p. 618 (2012).
Wilson et al., "Microbubble-Enhanced US in Body Imaging: What Role?," Radiology, vol. 257, No. 1, pp. 24-39 (Oct. 2010).

(56) References Cited

OTHER PUBLICATIONS

Wong et al., "Bubble Evolution in Acoustic Droplet Vaporization at Physiological Temperature via Ultra-high Speed Imaging," Soft Matter, vol. 7, pp. 4009-4016 (Jan. 2011).
Wong et al., "A Novel Method for Producing Partial Restriction Digestion of DNA Fragments by PCR with 5-methyl-CTP," Nucleic Acids Research, vol. 25, No. 20, pp. 4169-4171 (1997).
Wright et al., "Evaluation of New Thrombus-Specific Ultrasound Contrast Agent," Acad Radiol, vol. 5, (supp 1), pp. S240-S242 (1998).
Wu, "Sonograpic Demonstration of Duodenobiliary Reflux with Soda Enhancement," Journal of Clinical Ultrasound, vol. 32, No. 5, pp. 249-252 (Nov. 10, 2003).
Wu et al., "PSPICE Approach for Designing the Ultrasonic Piezoelectric Transducer for Medical Diagnostic Applications," Sensors and Actuators, vol. 75, pp. 186-198 (1999).
Xu et al., "Controllable Preparation of Monodisperse O/W and W/O Emulsions in the Same Microfluidic Device," Langmuir, vol. 22, No. 19, pp. 7943-7946 (Sep. 12, 2006).
Xu et al., "Generation of Monodisperse Particles by Using Microfluidics: Control Over Size, Shape, and Composition," Angew. Chem. Int. Ed., vol. 44, pp. 724-728 (2005).
Yasuda et al., "Using Acoustic Radiation Force as a Concentration Method for Erythrocytes," J. Acoust. Soc. Am., vol. 102, No. 1, pp. 642-645 (Jul. 1997).
Ye et al., "Microbubble Expansion in a Flexible Tube," Transactions of the ASME, vol. 128, pp. 554-563 (Aug. 2006).
Ye et al., "Direct Numerical Simulations of Micro-Bubble Expansion in Gas Embolotherapy," Journal of Biomedical Engineering, vol. 126, pp. 745-759 (Dec. 2004).
Zhang et al., "Acoustic Droplet Vaporization for Enhancement of Thermal Ablation by High Intensity Focused Ultrasound," Acad Radiol., vol. 18, No. 9, pp. 1-20 (Sep. 2011).
Zhang et al., "Initial Investigation of Acoustic Droplet Vaporization for Occulsion in Canine Kidney," Ultrasound Med Biol., vol. 36, No. 10, pp. 1-33 (Oct. 2010).
Zhang et al., "An in Vitro Study of a Phase-Shift Nanoemulsion: A Potential Nucleation Agent for Bubble-Enhanced HIFU Tumor Ablation," Ultrasound in Med. & Biol., vol. 36, No. 11, pp. 1856-1866 (2010).
Zhao et al., "Selective Imaging of Adherent Targeted Ultrasound Contrast Agents," Physics in Medicine and Biology, vol. 52, pp. 2055-2072 (2007).
Zhao et al., "Acoustic response from adherent targeted contrast agents," Journal of the Acoustical Society of America, vol. 120, No. 6, pp. 1-11 (2006).
Zhao et al., "Radiation-Force Assisted Targeting Facilitates Ultrasonic Molecular Imaging," Molecular Imaging, vol. 3, No. 3, pp. 135-148 (Jul. 2004).
Zheng et al., "A Novel Sensitive Targeted Imaging Technique for Ultrasonic Molecular Imaging," IEEE 2007 Ultrasonics Symposium, pp. 957-960 (2007).
Zheng et al., "Ultrasound-Driven Microbubble Oscillation and Translation Within Small Phantom Vessels," Ultrasound in Med. & Biol., vol. 33, No. 12, pp. 1978-1987 (2007).
Zhou et al., "The Size of Sonoporation Pores on the Cell Membrane," Ultrasound in Medicine & Biology, vol. 35, No. 10, pp. 1-10 (Oct. 2009).
Zipparo, "Mid-to High-Power Ultrasound Imaging Arrays—from ARFI to HIFU," IEEE 2003 Ultrasonics Symposium; Honolulu, Hawaii, pp. 684-688 (2003).
Fuciarelli et al., "Induction of Base Damage in DNA Solutions by Ultrasonic Cavitation," Free Radical Biology & Medicine, vol. 18, No. 2, pp. 231-238 (1995).
Notice of Allowance and Fee(s) Due for U.S. Appl. No. 15/880,481 (dated Aug. 8, 2019).
Non-Final Office Action for U.S. Appl. No. 15/247,840 (dated Oct. 5, 2018).
Final Office Action for U.S. Appl. No. 15/035,211 (dated Sep. 26, 2018).
Joneja et al., "A device for automated hydrodynamic shearing of genomic DNA," Biotechniques, vol. 46, pp. 1-7 (2009).
Dayton et al., "Application of Ultrasound to Selectively Localize Nanodroplets for Targeted Imaging and Therapy," Molecular Imaging, vol. 5, No. 3, pp. 1-32 (2006).
Janzen et al., "Advances in improving the quality and flexibility of compound management," Journal of Biomolecular Screening, vol. 14, No. 5, pp. 444-451 (2009).
Janzen et al., "A Chemogenonic Approach to Discovering Target Selective Drugs," Chemical Biology and Drug Design, vol. 67, Issue 1, pp. 85-86 (2006).
Kogan et al., "Microbubbles in Imaging: Applications Beyond Ultrasound," In Bubble Science, Engineering, and Technology, vol. 2, No. 1, pp. 1-11 (Jun. 2010).
Lipinski, "Lead-and Drug-like compounds: the rule-of-five revolution," Drug Discovery Today, vol. 1, pp. 337-341 (2004).
Macarron et al., "Impact of high-throughput screening in biomedical research," Nature Reviews Drug Discovery, vol. 10, pp. 188-195 (2011).
Marvel et al., "The Development and Validation of a LIPUS System with Preliminary Observations of Ultrasonic Effects on Human Adult Stem Cells," IEEE Transactions on Ultrasonics, Ferroelectrics, and Frequency Control, vol. 57, No. 9, pp. 1977-1984 (Sep. 2010).
Marvel et al., "Applications of Low Intensity Pulsed Ultrasound for Functional Bone Tissue Engineering using Adult Stem Cells," IEEE International Ultrasonics Symposium Proceedings, pp. 357-360 (2009).
Vedadi et al., "A chemical probe selectively inhibits G9a and GLP methyltransferase activity in cells," Nature Chemical Biology, vol. 7, No. 8, pp. 1-21 (Jul. 10, 2011).
Non-Final Office Action for U.S. Appl. No. 15/035,211 (dated Sep. 26, 2019).
Non-Final Office Action for U.S. Appl. No. 15/880,481 (dated Apr. 5, 2019).
Seo et al., "Microfluidic consecutive flow-focusing droplet generators," Soft Matter, vol. 3, pp. 986-992 (2007).
Applicant-Initiated Interview Summary for U.S. Appl. No. 15/247,840 (dated Oct. 25, 2019).
Advisory Action, Examiner-Initiated Interview Summary and AFCP 2.0 Decision for U.S. Appl. No. 15/035,211 (dated Mar. 7, 2019).
Non-Final Office Action for U.S. Appl. No. 15/247,840 (dated Jun. 13, 2019).
Fang et al., "Acoustically active perfluorocarbon nanoemulsions as drug delivery carriers for camptothecin: Drug release and cytotoxicity against cancer cells," Ultrasonics, vol. 49, pp. 39-46 (2009).
Final Office Action for U.S. Appl. No. 15/035,211 (dated May 1, 2020).
Liu et al., "Protein Lysine Methyltransferase G9a Inhibitors: Design, Synthesis, and Structure Activity Relationships of 2,4-Diamino-7-aminoalkoxy-quinazolines," J. Med. Chem., vol. 53, PMCID: PMC2920043, NIHMSID: NIHMS220759, pp. 5844-5857 (2011).
Mullin et al., "Effect of Anesthesia Carrier Gas on In-Vivo Circulation Times of Ultrasound Microbubble Contrast Agents in Rats," Contrast Media Mol Imaging, vol. 6, No. 3, pp. 1-14 (2011).
Final Office Action for U.S. Appl. No. 15/247,840 (dated Feb. 21, 2020).
Notice of Allowance and Fee(s) Due for U.S. Appl. No. 15/247,840 (dated May 17, 2021).
Commonly-Assigned, co-pending U.S. Appl. No. 17/198,926 for "Multi-Pillar Piezoelectric Stack Ultrasound Transducer and Methods for Using Same," (Unpublished, filed Mar. 11, 2021).
Goel et al., "Advances in Sonothrombolysis Techniques Using Piezoelectric Transducers," Sensors, vol. 20, pp. 1-17 (2020).
Goel et al., "Examining the Influence of Low-Dose Tissue Plasminogen Activator on Microbubble-Mediated Forward-Viewing Intravascular Sonothrombolysis," Ultrasound in Med. & Biol., vol. 46, No. 7, pp. 1-9 (2020).
Kim et al., "A Comparison of Sonothrombolysis in Aged Clots Between Low-Boiling-Point Phase-Change Nanodroplets and Microbubbles of the Same Composition," Ultrasound in Med. & Biol., vol. 46, No. 11, pp. 1-10 (2020).

(56) References Cited

OTHER PUBLICATIONS

Kim et al., "Miniaturized Intracavitary Forward-Looking Ultrasound Transducer for Tissue Ablation," IEEE Transactions on Biomedical Engineering, vol. 67, No. 7, pp. 1-10 (Jul. 2020).
Liu et al., "High-resolution intravascular MRI-guided perivascular ultrasound ablation," Magn Reson Med., vol. 83, pp. 1-14 (2020).
Ma et al., "Deep Penetration of Targeted Nanobubbles Enhanced Cavitation Effect on Thrombolytic Capacity," Bioconjugate Chem, vol. 31, pp. 1-6 (2020).
Non-Final Office Action for U.S. Appl. No. 15/247,840 (dated Oct. 6, 2020).
Commonly-Assigned, co-pending U.S. Appl. No. 17/016,304 for "Methods and Systems for Using Phase Change Nanodroplets to Enhance Sonothrombolysis," (Unpublished, filed Sep. 9, 2020).
Szablowski et al., "Achieving Spatial and Molecular Specificity with Ultrasound-Targeted Biomolecular Nanotherapeutics," Acc Chem Res., vol. 52, No. 9, pp. 1-17 (Sep. 17, 2019).
Zhang et al., "Sonothrombolysis with Magnetic Microbubbles Under a Rotational Magnetic Field," Ultrasonics, vol. 98, pp. 1-26 (Sep. 2019).
Li et al., "Spontaneous Nucleation of Stable Perfluorocarbon Emulsions for Ultrasound Contrast Agents," Nano Lett., vol. 19, pp. 1-9 (2019).
Rojas et al., "Vaporization Detection Imaging: A Technique for Imaging Low-Boiling-Point Phase-Change Contrast Agents with a High Depth of Penetration and Contrast-to-Tissue Ratio," Ultrasound in Med. & Biol., vol. 45, No. 1, pp. 1-16 (2019).
Guo et al., "Reduced clot debris size in sonothrombolysis assisted with phase-change nanodroplets," Ultrasonics—Sonochemistry, vol. 54, pp. 1-9 (2019).
Engelberger et al., "Enhanced Thrombolysis by Ultrasound-Assisted Catheter-Directed Thrombolysis and Microbubbles in an In Vitro Model of Iliofemoral Deep Vein Thrombosis," Thrombosis and Haemostasis, vol. 119, No. 7/2019, pp. 1094-1101 (Jun. 5, 2019).
Vanhille et al., "Numerical Simulations of the Nonlinear Interaction of a Bubble Cloud and High Intensity Focused Ultrasound Field," Acoustics, vol. 1, pp. 1-12 (2019).
Wu et al., "Focused Ultrasound-Facilitated Brain Drug Delivery Using Optimized Nanodroplets: Vaporization Efficiency Dictates Large Molecular Delivery," Phys Med Biol., vol. 63, No. 3, pp. 1-24 (2019).
Suo et al., "Dynamic assessment of dual-frequency microbubble-mediated sonothrombolysis in vitro," Journal of Applied Physics, vol. 125, pp. 1-11 (Feb. 26, 2019).
Zhong et al., "Low-Intensity Focused Ultrasound-Responsive Phase-Transitional Nanoparticles for Thrombolysis without Vascular Damage: A Synergistic Nonpharmaceutical Strategy," ACS Nano, vol. 13, pp. 1-17(2019).
Shi et al., "Integrated histotripsy and bubble coalescence transducer for thrombolysis," Ultrasound Med Biol., vol. 44, No. 12, pp. 1-27 (Dec. 2018).
Brubler et al., "Nanoscaled ultrasound contrast agents for enhanced sonothrombolysis," Colloids and Surfaces B: Biointerfaces, vol. 172, pp. 1-6 (2018).
Mazzolai et al., "Diagnosis and management of acute deep vein thrombosis: a joint consensus document from the European Society of Cardiology working groups of aorta and peripheral vascular diseases and pulmonary circulation and right ventricular function," European Heart Journal, vol. 39, pp. 1-14 (2018).
Goudot et al., "Pulsed cavitational therapy using high-frequency ultrasound for the treatment of deep vein thrombosis in an in vitro model of human blood clot," Physics in Medicine and Biology, vol. 62, No. 24, pp. 1-26 (2017).
Zhang et al., "Noninvasive Thrombolysis using Microtripsy in a Porcine Deep Vein Thrombosis Model," Ultrasound Med Biol., vol. 43, No. 7, pp. 1-27 (Jul. 2017).
Kim et al., "Intravascular forward-looking ultrasound transducers for microbubble-mediated sonothrombolysis," Scientific Reports, vol. 7, No. 3454, pp. 1-10 (Jun. 14, 2017).
Suo et al., "Microbubble mediated dual-frequency high intensity focused ultrasound thrombolysis: An In vitro study," Appl. Phys. Lett., vol. 110, pp. 1-5 (Jan. 10, 2017).
Fix et al., "An evaluation of the sonoporation potential of low-boiling point phase-change ultrasound contrast agents in vitro," Journal of Therapeutic Ultrasound, vol. 5, No. 7, pp. 1-11 (2017).
Yang et al., "Effect of pulse repetition frequency of high-intensity focused ultrasound on in vitro thrombolysis," Ultrasonics Sonochemistry, vol. 35, pp. 1-9 (2017).
Escoffre et al., "Therapeutic Ultrasound," Advances in Experimental Medicine and Biology, vol. 880, pp. 1-15 (2016).
Song et al., "Ultrasound Triggered Tumor Oxygenation with Oxygen-Shuttle Nanoperfluorocarbon to Overcome Hypoxia-Associated Resistance in Cancer Therapies," Nano Lett., vol. 16, pp. 1-9 (2016).
Chu et al., "Focused Ultrasound-Induced Blood-Brain Barrier Opening: Association with Mechanical Index and Cavitation Index Analyzed by Dynamic Contrast-Enhanced Magnetic-Resonance Imaging," Nature, Scientific Reports, vol. 6, No. 33264, pp. 1-13 (Sep. 15, 2016).
Zhang et al., "Histotripsy Thrombolysis on Retracted Clots," Ultrasound Med Biol., vol. 42, No. 8, pp. 1-35 (Aug. 2016).
Bader et al., "Efficacy of histotripsy combined with rt-PA in vitro," Phys Med Biol., vol. 61, No. 14, pp. 1-35 (Jul. 21, 2016).
DiNisio et al., "Deep vein thrombosis and pulmonary embolism," Lancet, vol. 388, pp. 1-14 (Jun. 30, 2016).
Luke et al., "Super-Resolution Ultrasound Imaging in Vivo with Transient Laser-Activated Nanodroplets," Nano Lett., vol. 16, No. 4, pp. 1-9 (Apr. 13, 2016).
Zhang et al., "Histotripsy Thrombolysis on Retracted Clots," Ultrasound in Med. & Biol., vol. 42, No. 8, pp. 1-16 (2016).
Streiff et al., "Guidance for the treatment of deep vein thrombosis and pulmonary embolism," J Thromb Thrombolysis, vol. 41, pp. 1-36 (2016).
Watson et al., "Thrombolysis for accurate deep vein thrombosis," Cochrane Database of Systematic Reviews, vol. 11, pp. 1-62 (2016).
Zhang et al., "Non-invasive Thrombolysis using Microtripsy: A Parameter Study," IEEE Trans Ultrason Ferroelectr Freq Control., vol. 62, No. 12, pp. 1-34 (Dec. 2015).
Dixon et al., "Microbubble-Mediated Intravascular Ultrasound Imaging and Drug Delivery," IEEE Transactions on Ultrasonics, Ferroelectrics, and Frequency Control, vol. 62, No. 9, pp. 1-12 (Sep. 2015).
Heit, "Epidemiology of venous thromboembolism," Nat Rev Cardiol., vol. 12, No. 8, pp. 1-27 (Aug. 2015).
Sen et al., "Mechanical Index," Anatol J Cardiol, vol. 15, pp. 334-336 (2015).
Zhang et al., "Non-invasive Thrombolysis using Histotripsy beyond the "Intrinsic" Threshold (Microtripsy)," IEEE Trans Ultrason Ferroelectr Feq Control., vol. 62, No. 7, pp. 1-35 (Jul. 2015).
Acconcia et al., "The Effect of Short Duration Ultrasound Pulses on the Interaction Between Individual Microbubbles and Fibrin Clots," Ultrasound in Med. & Biol., vol. 41, No. 10, pp. 1-9 (2015).
Engelberger et al., Ultrasound-Assisted Versus Conventional Catheter-Directed Thrombolysis for Acute Iliofemoral Deep Vein Thrombosis, Circ Cardiovasc Interv, pp. 1-9 (2015).
Kim et al., "Phantom evaluation of stacked-type dual-frequency 1-3 composite transducers: A feasibility study on intracavitary acoustic angiography," Ultrasonics, vol. 63, pp. 1-9 (2015).
Lindsey et al., "On the relationship between microbubble fragmentation, deflation, and broadband superharmonic signal production," Ultrasound Med Biol., vol. 41, No. 6, pp. 1-30 (Jun. 2015).
Moyer et al., "High-intensity focused ultrasound ablation enhancement in vivo via phase-shift nanodroplets compared to microbubbles," Journal of Therapeutic Ultrasound, vol. 3, No. 7, pp. 1-9 (2015).
Li et al., "Quantifying Activation of Perfluorocarbon-Based Phase-Change Contrast Agents Using Simultaneous Acoustic and Optical Observation," Ultrasound Med Biol., vol. 41, No. 5, pp. 1-20 (May 2015).
Suo et al., "Thrombolysis using multi-frequency high intensity focused ultrasound at MHz range: an in vitro study," Phys. Med. Biol., vol. 60, pp. 1-17 (2015).

(56) References Cited

OTHER PUBLICATIONS

Xu et al., "Dependence of pulsed focused ultrasound induced thrombolysis on duty cycle and cavitation bubble size distribution," Ultrasonics Sonochemistry, vol. 22, pp. 1-7 2015).
Johnston et al., "Mechanical characterization of bulk Sylgard 184 for microfluidics and microengineering," J. Micromech. Microeng., vol. 24, pp. 1-9 (2014).
Pajek et al., "High intensity focused ultrasound sonothrombolysis: the use of perfluorocarbon droplets to achieve clot lysis at reduced acoustic powers," Ultrasound Med Biol., vol. 40, No. 9, pp. 1-22 (Sep. 2014).
Acconcia et al., "Interactions Between Individual Ultrasound-Stimulated Microbubbles and Fibrin Clots," Ultrasound in Med. & Biol., vol. 40, No. 9, pp. 1-17 (2014).
Owings, "FDA Clears EKOS EkoSonic Endovascular System," FDA News, www.fdanews.com/articles/164759-fda-clears-ekos-ekosonic-endovascular-system, pp. 1-2 (May 27, 2014).
Kim et al., "Homogenization of PMN-PT/epoxy 1-3 piezocomposites by resonator measurements and finite element analysis ," Sensors and Actuators A, vol. 206, pp. 1-10 (2014).
Pajek et al., "High-Intensity Focused Ultrasound Sonothrombolysis: The Use of Perfluorocarbon Droplets to Achieve Clot Lysis at Reduced Acoustic Power," Ultrasound in Med. & Biol., vol. 40, No. 9, pp. 1-11 (2014).
Shaw et al., "Pathophysiological mechanisms of high-intensity focused ultrasound-mediated vascular occlusion and relevance to non-invasive fetal surgery," J. R. Soc. Interface, vol. 11, pp. 1-17 (2014).
Dixon et al., "Enhanced Intracellular Delivery of a Model Drug Using Microbubbles Produced by a Microfluidic Device," Ultrasound in Med. & Biol., vol. 39, No. 7, pp. 1-10 (2013).
Holscher et al., "Effects of varying duty cycle and pulse width on high-intensity focused ultrasound (HIFU)-induced transcranial thrombolysis," Journal of Therapeutic Ultrasound, vol. 1, No. 18, pp. 1-5 (2013).
Ma et al., "Design, Fabrication, and Characterization of a Single-Aperture 1,5-MHz/3-MHz Dual-Frequency HIFU Transducer," IEEE Transactions of Ultrasonics, Ferroelectrics, and Frequency Control, vol. 60, No. 7, pp. 1-12 (Jul. 2013).
Sutton et al. "Clot retraction affects the extent of ultrasound-enhanced thrombolysis in an ex vivo porcine thrombosis model," Ultrasound Med Biol., vol. 39, No. 5, pp. 1-23 (May 2013).
Galanaud et al., "The history and historical treatments of deep vein thrombosis, "Journal of Thrombosis and Haemostasis, vol. 11, pp. 1-10 (2013).
Sommer et al., "Applicators for MR-Guided Ultrasonic Ablation of BPH," Invest Radiol., vol. 48, No. 6, pp. 1-18 (Jun. 2013).
Zhao et al., "Potential and problems in ultrasound-responsive drug delivery systems," International Journal of Nanomedicine, pp. 1-14 (Apr. 2013).
Li et al., "Development of Piezoelectric Ultrasonic Thrombolysis Device for Blood Clot Emulsification," International Scholarly Research Network, vol. 2012, pp. 1-7 (2012).
Ballehaninna et al., "Acute superior mesenteric artery embolism: reperfusion with AngioJet hydrodynamic suction thrombectomy and pharmacologic thrombolysis with the EKOS catheter," Vascular, vol. 20, No. 3, pp. 166-170 (2012).
Burgess et al., "High-Intensity Focused Ultrasound (HIFU) for Dissolution of Clots in a Rabbit Model of Embolic Stroke," PLoS ONE, vol. 7, No. 8, pp. 1-7 (Aug. 2012).
Jin et al., "Ultrasound-triggered thrombolysis using urokinase-loaded nanogels," International Journal of Pharmaceutics, vol. 434, pp. 1-7 (2012).
Wright et al., "In Vitro and In Vivo High Intensity Focused Ultrasound Thrombolysis," Invest Radiol., vol. 47, No. 4, pp. 1-25 (Apr. 2012).
Holscher et al., "Noninvasive Transcranial Clot Lysis Using High Intensity Focused Ultrasound," J Neurol Neurophysiol, pp. 1-7 (2011).

Maxwell et al., "Cavitation clouds created by shock scattering from bubbles during histotripsy," J. Acoust. Soc. Am., vol. 130, No. 4, pp. 1888-1898 (Oct. 2011).
Previtali et al., "Risk factors for venous and arterial thrombosis," Blood Transfus., vol. 9, pp. 1-19 (2011).
Sheeran et al., "Formulation and Acoustic Studies of a New Phase-Shift Agent for Diagnostic and Therapeutic Ultrasound," Langmuir, vol. 27, No. 17, pp. 1-23 (Sep. 6, 2011).
Galiuto et al., "The EAE Textbook of Echocardiography," European Society of Cardiology, 2 ed., pp. 1-37 (May 2011).
Karthikesalingam et al., "A Systematic Review of Percutaneous Mechanical Thrombectomy in the Treatment of Deep Venous Thrombosis," Eur J Vase Endovasc Surg, vol. 41, pp. 1-12 (2011).
Mast et al., "Treatment of Rabbit Liver Cancer In Vivo Using Miniaturized Image-Ablate Ultrasound Arrays," Ultrasound in Med. & Biol., vol. 37, No. 10, pp. 1-13 (2011).
Beckman et al., "Venous Thromboembolism A Public Health Concern," Am J Prev Med, vol. 38, No. 4S, pp. 1-7 (2010).
Kuo et al., "Catheter-directed Therapy for the Treatment of Massive Pulmonary Embolism: Systematic Review and Meta-analysis of Modern Techniques," J Vasc Interv Radiol, vol. 20, pp. 1-10 (2009).
Robert-Ebadi et al., "Use of anticoagulants in elderly patients: practical recommendations," Clinical Interventions in Aging, vol. 4, pp. 165-178 (2009).
"Safety and Effectiveness of a New Generation of Mechanical Devices for Clot Removal in Intracranial Large Vessel Occlusive Disease," The Penumbra Pivotal Stroke Trial, pp. 1-8 (2009).
Datta et al., "Ultrasound-enhanced thrombolysis using Definity as a cavitation nucleation agent," Ultrasound Med Biol., vol. 34, No. 9, pp. 1-24 (Sep. 2008).
Chopra et al., "MRI-compatible transurethral ultrasound system for the treatment of localized prostate cancer using rotational control," Med. Phys., vol. 35, No. 4, pp. 1-13 (Apr. 2008).
Owens, "Ultrasound-Enhanced Thrombolysis: EKOS EndoWave Infusion Catheter System," Seminars in Interventional Radiology, vol. 25, No. 1, pp. 1-5 (2008).
Prokop et al., "Cavitational Mechanisms in Ultrasound-Accelerated Fibrinolysis," Ultrasound in Med. & Biol., vol. 33, No. 6, pp. 1-10 (2007).
Van Ha, "Complications of Inferior Vena Caval Filters," Seminars in Interventional Radiology, vol. 23, No. 2, pp. 1-6 (2006).
Melodelima et al., "Transoesophageal Ultrasound Applicator for Sector-Based Thermal Ablation: First In Vivo Experiments," Ultrasound in Med. & Biol., vol. 29, No. 2, pp. 1-7 (2003).
Greenfield et al., "Recurrent thromboembolism in patients with vena cava filters," Journal of Vascular Surgery, vol. 33, No. 3, pp. 510-514 (2001).
Goodman, "Toward Evidence-Based Medical Statistics. 1: The P Value Fallacy," Ann Intern Med., pp. 995-1004 (1999).
Tachibana et al., "Albumin Microbubble Echo-Contrast Material as an Enhancer for Ultrasound Accelerated Thrombolysis," Circulation, vol. 92, No. 5, pp. 1-7 (1995).
Mills et al., "Multi-Layered PZT/Polymer Composites to Increase Signal-to-Noise Ratio and Resolution for Medical Ultrasound Transducers Part II: Thick Film Technology," IEEE Transactions on Ultrasonics, Ferroelectrics, and Frequency Control, vol. 49, No. 7, pp. 1005-1014 (Jul. 2002).
Fan et al., "Nonlinear Constitutive Behavior of Soft and Hard PZT: Experiments and Modeling," Acta mater., vol. 47, No. 17, pp. 4415-4425 (1999).
Anderson et al., "A Population-Based Perspective of the Hospital Incidence and Case-Fatality Rates of Deep Vein Thrombosis and Pulmonary Embolism," Arch Intern Med, vol. 151, pp. 1-6 (May 1991).
Sponer, "Theoretical estimation of the cavitation threshold for very short pulses of ultrasound," Ultrasonics, vol. 29, pp. 376-380 (Sep. 1991).
Stone et al., "Pulsed-high intensity focused ultrasound enhanced tPA mediated thrombolysis in a novel in vivo clot model, a pilot study," Thromb Res., vol. 121, No. 2, pp. 1-15 (2007).
Datta et al., "Correlation of Cavitation with Ultrasound Enhancement of Thrombolysis," Ultrasound Med Biol., vol. 32, No. 8, pp. 1-20 (Aug. 2006).

(56) References Cited

OTHER PUBLICATIONS

Mitragotri, "Healing sound: the use of ultrasound in drug delivery and other therapeutic applications," Drug Discovery, vol. 4, pp. 1-6 (Mar. 2005).
Kahn, "The Clinical Diagnosis of Deep Venous Thrombosis," Arch Intern Med., vol. 158, pp. 1-9 (Nov. 23, 1998).
Notification of Transmittal of the International Search Report and the Written Opinion of the International Searching Authority, or the Declaration of International Application No. PCT/US17/42372 (dated Nov. 24, 2017).
Heidt et al., "Molecular Imaging of Activated Platelets Allows the Detection of Pulmonary Emoblism with Magnetic Resonance Imaging," Sci. Rep., vol. 6, pp. 25044 (2016).
Dilektasli et al., "Catheter-Directed Therapy in Acute Pulmonary Embolism with Right Ventricular Dysfunction: A Promising Modality to Provide Early Hemodynamic Recovery," Med. Sci. Monit., vol. 22, pp. 1265-1273(2016).
Fan et al., "Tissue Plasminogen Activator Neurotoxicity is Neutralized by Recombinant ADAMTS 13," Sci. Rep., vol. 6, pp. 25971 (2016).
Porter et al., "Diagnostic ultrasound high mechanical index impulses restore microvascular flow in peripheral arterial thromboembolism," Ultrasound Med. Biol., vol. 42, pp. 1531-1540 (2016).
Roberts et al., "Quantitative assessment of placental perfusion by contrast-enhanced ultrasound in macaques and human subjects," Am. J. Obstet. Gynecol, vol. 214, pp. 369.e1-369e8 (2016).
Shelton et al., "Molecular Acoustic Angiography: A New Technique for High-resolution Superharmonic Ultrasound Molecular Imaging," Ultrasound Med. Biol. vol. 42, pp. 769-781 (2016).
Porter et al., "Ultrasound, microbubbles, and thrombolysis," Prog. Cardiovasc. Dis., vol. 44, pp. 101-110 (2001).
Belcik et al., "Augmentation of limb perfusion and reversal of tissue ischemia produced by ultrasound-mediated microbubble cavitation," Circ. Cardiovasc. Imaging, vol. 8, pp. e002979 (2015).
Bader et al., "Shaken and Stirred: Mechanisms of Ultrasound-Enhanced Thrombolysis," Ultrasound Med. Biol., vol. 41, pp. 187-196 (2015).
Hsieh et al., "A laser ultrasound transducer using carbon nanofibers-polydimethylsiloxane compsite thin film," Applied Physics Letters, vol. 106, No. 2, pp. 021902 (2015).
Kuo et al., "Pulmonary embolism response to fragmentation, embolectomy, and catheter thrombolysis (PERFECT): Initial results from a prospective multicenter registry," Chest, vol. 148, pp. 667-673 (2015).
Pacella et al., "Treatment of microvascular micro-embolization using microbubbles and long-tone-burst ultrasound: An invivo study," Ultrasound Med. Biol., vol. 41, pp. 456-464 (2015).
Sista et al., "Catheter-Directed Thrombolysis for Pulmonary Embolism," JACC Cardiovasc. Interv., vol. 8, pp. 1393-1395 (2015).
Wolberg et al., "Venous thrombosis," Nat. Rev. Dis. Prim, vol. 1, pp. 15006 (2015).
Chatterjee et al., "Thrombolysis for pulmonary embolism and risk of all-cause mortality, major bleeding, and intracranial hemorrhage: a meta-analysis," JAMA, vol. 311, pp. 2414-2421 (2014).
Kucher et al., "Randomized, controlled trial of ultrasound-assistaed catheter-directed thrombolysis for acute intermediate-risk pulmonary embolism," Circulation, vol. 129, pp. 479-486 (2014).
Fanikos et al., "Hospital costs of acute pulmonary embolism," Am. J. Med., vol. 126, pp. 127-132 (2013).
Xu et al., "Energy harvesting using a PZT ceramic multilayer stack," Smart Mater. Struct., vol. 22, pp. 65015 (2013).
Bolognese et al., "Real-Time Ultrasound Perfusion Imaging in Acute Stroke: Assessment of Cerebral Perfusion Deficits Related to Arterial Recanalization," resoundund Med. Biol., vol. 39, pp. 745-752 (2013).
Bader et al., "Gauging the likelihood of stable cavitation from ultrasound contrast agents," Phys. Med. Biol., vol. 58, pp. 127-144 (2013).
Weiss et al., "Mechanical clot damage from cavitation during sonothrombolysis," J. Acoust. Soc. Am., vol. 133, pp. 3159-3175 (2013).
Kearon et al., "Antithrombotic therapy for VTE disease: Antithrombotic therapy and prevention of thrombosis, 9th ed: American College of Chest Physicians evidence-based clinical practice guidelines," Chest, vol. 141, pp. e419s-e496s (2012).
Kutty et al., "Microbubble Mediated Thrombus Dissolution with Diagnostic Ultrasound for the Treatment of Chronic Venous Thrombi," PLoS One 7, pp. e51453 (2012).
Goldhaber et al., "Pulmonary embolism and deep vein thrombosis," Lancet, vol. 379, pp. 1835-1846 (2012).
Slikkerveer et al., "Ultrasound enhanced prehospital thrombolysis using microbubbles infusion in pateitns with acute st elevation myocardial infarction: Pilot of the sonolysis study," Ultrasound Med. Biol., vol. 38, pp. 247-252 (2012).
Popovic et al., Massive pulmonary embolism: Percutaneous emergency treatment using an aspirex thrombectomy catheter, Cardiovasc. Intervent. Radiol., vol. 33, pp. 1052-1055 (2010).
MacDougall et al., "Economic burden of deep-vein thrombosis, pulmonary embolism, and postthrombotic syndrome," Am. J. Heal. Pharm., vol. 63, pp. S5-S15 (2006).
Cesarman-Maus et al., "Molecular mechanisms of fibrinolysis," Br. J. Haematol., vol. 129, pp. 307-321 (2005).
Schafer et al., "Influence of ultrasound operating parameters on ultrasound-induced thrombolysis in vitro," Ultrasound Med. Biol., vol. 31, pp. 841-847 (2005).
Dijkmans et al., "Microbubbles and ultrasound: From diagnosis to therapy," Eur. J. Echocardiogr., vol. 5, pp. 245-256 (2004).
Postema et al., "Ultrasound-induced microbubble coalescence," Ultrasound Med. Biol, vol. 30, pp. 1337-1344 (2004).
Mahon et al., "North American clinical experience with the EKOS MicroLysUS infusion catheter for the treatment of embolic stroke," Am. J. Neuroradiol., vol. 24, pp. 534-538 (2003).
Hill et al., "Physical principles of medical ultrasonics," John Wiley & Sons, Chapter 2, pp. 41-59 (2004).
Blinc et al., "Characterization of Ultrasound-Potentiated Fibrinolysis," In Vitro, vol. 8, pp. 2636-2643 (1993).
Gersh et al., "The spatial dynamics of fibrin clot dissolution catalyzed by erythrocyte-bound vs. free fibrinolytics," J. Thromb. Haemost., vol. 8, pp. 1066-1074 (2010).
Goldhaber et al., "Pulmonary embolism and deep vein thrombosis," Circulation, vol. 106, pp. 1436-1438 (2002).
Francis, "Ultrasound-enhanced thrombolysis," Echocardiography, vol. 18, pp. 239-246 (2001).
Atar et al., "Ultrasonic Thrombolysis: Catheter-delivered and transcutaneous applications," Euro. J. Ultrasound, vol. 9, pp. 39-54 (1999).

\* cited by examiner

METHODS AND SYSTEMS FOR USING ENCAPSULATED MICROBUBBLES TO PROCESS BIOLOGICAL SAMPLES

PRIORITY CLAIM

This application is a divisional of U.S. patent application Ser. No. 14/432,747, filed Mar. 31, 2015, which is a National Stage Entry of International Patent Application No. PCT/US2013/063397, filed Oct. 4, 2013, which claims the benefit of U.S. Provisional Patent Application Ser. No. 61/709,488, filed Oct. 4, 2012.

GOVERNMENT SUPPORT

This invention was made with government support under Grant Numbers EB008733 and EB009066 awarded by the National Institutes of Health. The government has certain rights in the invention.

TECHNICAL FIELD

The subject matter described herein relates to methods and systems for processing biological samples. More particularly, the subject matter described herein relates to methods and systems for using encapsulated microbubbles to process biological samples.

BACKGROUND

The transformation of a normal cell into a cancer cell is the result of an accumulation of genetic mutations or epigenetic changes that lead to aberrant gene expression. Understanding where and when these changes occur in any given tumor type is a primary focus of cancer research. Since cellular transformation is often unique for each patient, a diagnostic test that provides a customized genome-based profile of a tumor is very desirable and is likely be a standard in the future of oncological medicine. Genetic mutations in transformed cells are now very commonly profiled using next-generation sequencing (NGS). Incorporation of NGS technology into routine clinical diagnostics, however, will require overcoming a number of hurdles including streamlining of sample processing.

Random, unbiased fragmentation of DNA is necessary for NGS and is a key step in building any genomic library for sequencing. When NGS is used to determine genetic changes, the desired length of each DNA fragment in base pairs (bp) depends on the maximum possible read length of the sequencer. If fragments exceed the maximum length, they will be incompletely read. If they are too small, or degraded, then they will be excluded from the read. Therefore, consistent DNA fragmentation is required for quality NGS data. DNA shearing is also used in processes such as chromatin immunoprecipitation (ChIP), formaldehyde-assisted interrogation of regulatory elements (FAIRE), and DNA sequencing. For each of these techniques, it is important that DNA is sheared to a consistent size in the shortest time possible. Chromatin from cells that have been subjected to formaldehyde crosslinking (e.g., from the ChIP and FAIRE techniques), are particularly resistant to conventional DNA shearing techniques. Thus, the time required to shear formaldehyde cross-linked DNA makes it difficult to integrate this step into automated protocols with large sample sets.

Conventional methods for fragmentation of DNA include enzymatic digestion, sonication, nebulization, and hydrodynamic shearing. While all of these techniques are widely used, each has advantages and disadvantages. Enzymatic digestion using DNase I, MNase, or restriction enzymes is very efficient, but introduces an enzyme bias. Regions of transcriptionally silent, tightly packed (heterochromatic) DNA and DNA with high G-C content can be refractive to enzymatic digestion and many enzymes only create nicks in the DNA instead of cutting completely though both strands. The nebulization process shears solubilized DNA by forcing it through a pressurized nozzle (atomization). This method is fast, but requires large quantities of DNA and often results in a large distribution in the DNA fragment size and cross-contamination between samples. Hydrodynamic shearing involves forcing solubilized DNA through a mesh. It has the advantage of rapidly producing small DNA fragments of nearly uniform length. This method, however, is costly and the screen used for shearing is prone to clogging and cross-contamination between samples. Similar to enzymatic digestion, heterochromatic DNA or DNA with high G-C content are very difficult to shear, which creates a bias toward better shearing efficiency in euchromatic and A-T rich regions. Although NGS involves fragmentation of purified genomic DNA, ChIP requires fragmentation of DNA from the nuclei of intact, formaldehyde cross-linked cells. Formaldehyde crosslinks protein to DNA, and as a result cells are very rigid and particularly resistant to lysis. Therefore, DNA fragmentation for fixed samples such as ChIP or FFPE tissue is even more challenging. The summary is that current DNA fragmentation methods are a bottleneck for diagnostic assays such as NGS and ChIP, and that a substantial improvement in methods for DNA fragmentation would have a significant impact.

Presently, DNA fragmentation in academic laboratories is commonly performed using a probe-based or acoustic sonicator. Sonication uses uncontrolled cavitation to shear DNA. Conventional DNA sonicators range from a single probe to multi-sample acoustic water bath sonicators. The method typically produces inconsistent results and is time consuming, thereby limiting its utility. DNA extracted from cells or tissue must be optimized each time to ensure that fragmentation occurs to the desired size range. In the case of formaldehyde cross-linked samples, checking DNA fragment size involves an overnight incubation, so optimization can take several days for each sample type. Therefore, an inexpensive method that provides shearing consistency independent of cell or tissue type and that can be performed rapidly would be very valuable and would have a significant impact on the use of technologies like NGS as a companion diagnostic for cancer.

There are few methods currently available to increase DNA fragmentation efficiency by an acoustic or probe sonicator. Borosilicate glass beads are sometimes added to the DNA mix during sonication, but these beads provide limited improvement and will reduce the lifetime of a probe sonicator by causing pitting in the probe. Another technique uses a vial that contains a rod that enucleates bubbles during sonication. Cavitation nucleated from this rod help to shear DNA. While these microbubble nucleating rods improve consistency results in the sonicator, they release plastic residue that can clog columns in downstream applications, and are very costly (five dollars per sample). Thus, current DNA fragmentation methods are a bottleneck for the creation of NGS libraries.

Accordingly, in light of these disadvantages associated with conventional techniques for DNA shearing, there exists a need for more consistent and efficient techniques for DNA shearing. More specifically, there exists a need for methods and systems for using encapsulated microbubbles to process biological samples.

SUMMARY

According to one aspect, the subject matter described herein includes a method for using encapsulated microbubbles to process a biological sample according to an embodiment of the subject matter described herein. The method includes creating a mixture comprising encapsulated microbubbles mixed with a biological sample and adding activation energy to the mixture to cause at least some of the microbubbles to oscillate or burst and thereby process the sample.

According to another aspect, the subject matter described herein includes a system for delivering a solution of microbubbles to a biological sample according to an embodiment of the subject matter described herein. The system includes a container for holding the solution of microbubbles and at least one outlet for delivering the solution of microbubbles to a biological sample.

According to yet another aspect, the subject matter described herein includes a system for delivering microbubbles to a biological sample according to an embodiment of the subject matter described herein. The system includes a container for holding a solution that will formulate encapsulated microbubbles when processed and at least one outlet for delivering the solution to a biological sample.

The subject matter described herein can be implemented in software in combination with hardware and/or firmware. For example, the subject matter described herein can be implemented in software executed by a processor. In one exemplary implementation, the subject matter described herein can be implemented using a non-transitory computer readable medium having stored thereon computer executable instructions that when executed by the processor of a computer control the computer to perform steps. Exemplary computer readable media suitable for implementing the subject matter described herein include non-transitory computer-readable media, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

BRIEF DESCRIPTION OF THE DRAWINGS

Preferred embodiments of the subject matter described herein will now be explained with reference to the accompanying drawings, wherein like reference numerals represent like parts, of which.

DETAILED DESCRIPTION

Figure 1:
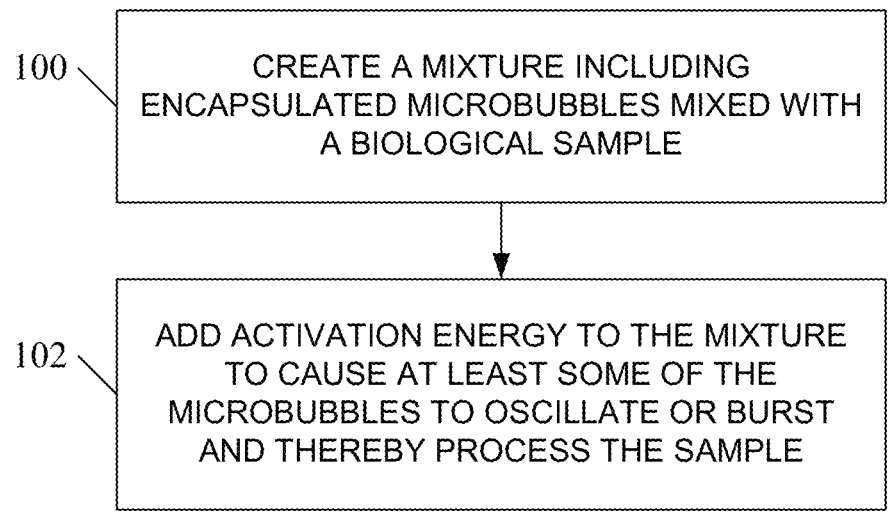
FIG. 1 is a flow chart illustrating an exemplary process for using encapsulated microbubbles to process a biological sample according to yet another embodiment of the subject matter described herein.

In accordance with the subject matter disclosed herein, methods and systems for using encapsulated microbubbles to process biological samples are provided. The addition of controlled sized lipid microbubbles to an acoustic sonication process significantly improves the efficiency and consistency of DNA fragmentation and the presence of the lipid microbubbles does not interfere with downstream fluorescence-based analyses such as quantitative PCR. This technique can be used to greatly improve sample processing efficiency and robustness. Microbubbles may also be used to enhance other sample processes, such as to effect cell lysis, to perform tissue dispersion, and to detach tissues from tissue culture (TC) plates in preparation for transfer of tissue to polymerase chain reaction (PCR) plates.

Reference will now be made in detail to exemplary embodiments of the present invention, examples of which are illustrated in the accompanying drawings. Wherever possible, the same reference numbers will be used throughout the drawings to refer to the same or like parts.

Microbubbles, which are bubbles that are typically in the 1-10 micron diameter size range, have been used in medical diagnostics as contrast agents for ultrasound imaging for approximately two decades. For medical applications, these microbubbles utilize an encapsulating shell, typically a lipid, and high molecular weight gas core to maximize stability. The highly compressible core of a gas filled microbubble enables it to compress and expand in a pressure field. In an acoustic field, this oscillation happens at the frequency of the sound wave. For medical acoustics, this is on the order of megahertz (MHz). It has been shown through the use of high-speed photography that expansion and compression velocity of microbubbles in an acoustic field can be on the order of 350 meters per second even at only moderate acoustic pressures (2.4 MHz, 1.2 megapascals (MPa)). When the bubble remains intact, this phenomenon is called stable cavitation. At higher acoustic energies, these microbubbles can oscillate to such a violent extent that the bubbles will break up in a process called transient cavitation.

Cavitation in general is a very mechanically vigorous process, and the intensity typically increases as acoustic pressure is increased and acoustic center frequency is decreased. At sufficient acoustic parameters microbubble-mediated cavitation is well known to cause various effects such as the disruption of cell membranes, the breakup up of blood clots, and the permeabilization of vascular endothelium. The exact mechanism is still poorly understood, however. Furthermore, because microbubbles are orders of magnitude larger in size than DNA base pairs, it was not known whether microbubbles would perform as an effective reagent for DNA fragmentation in an acoustic sonicator. Since the microbubbles consist of a lipid layer surrounding an inert gas, and they were used in small quantities (10 micrograms (4) per sample), they were not expected to interfere with downstream analyses such as the fluorescent-based quantitative polymerase chain reaction (qPCR), NGS, or ChIP, however, and were therefore a good candidate for study.

FIG. 1 is a flow chart illustrating an exemplary process for using encapsulated microbubbles to process a biological sample according to yet another embodiment of the subject matter described herein. In the embodiment illustrated in FIG. 1, step 100 includes creating a mixture that contains encapsulated microbubbles mixed with a biological sample, and step 102 includes adding activation energy to the mixture to cause at least some of the microbubbles to oscillate or burst, thereby processing the sample. In one embodiment, a majority of the microbubbles have a diameter in the range from 0.1 microns to 10 microns.

The inclusion of microbubbles into a biological sample and their subsequent activation has been found to increase the efficiency of a number of processes. For example, the biological sample may include DNA or DNA that has been cross-linked to protein, in which case processing the sample may include shearing the DNA. The biological sample may include cells, including but not limited to bacteria or yeast cells, where processing the sample may include effecting cell lysis. The biological sample may include tissue, in which case processing the sample includes performing tissue dispersion. The method may be successfully applied to a variety of types of tissues, including fresh tissue, cryogenically preserved tissue, and fixed and paraffin embedded tissue.

There are a number of ways in which activation energy may be added to the mixture, including but not limited to sonicating the mixture, exposing the mixture to laser light, and exposing the mixture to heat. Sonicating the mixture may include applying sonic energy in the 0.01 MHz to 10.0 MHz frequency range.

There are a number of ways to create the biological sample and microbubble mixture. Some of these are illustrated in FIGS. 2, 3, and 4.

Figure 2:
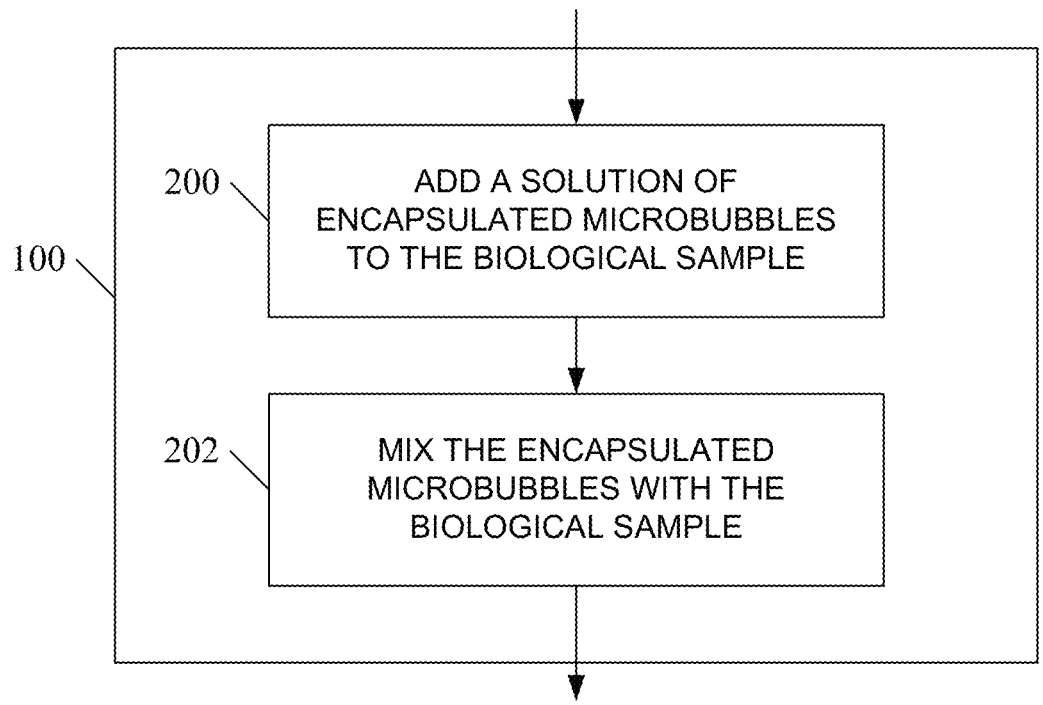
FIG. 2 is a flow chart illustrating a method for creating the biological sample and microbubble mixture according to an embodiment of the subject matter described herein.

FIG. 2 is a flow chart illustrating a method for creating the biological sample and microbubble mixture according to an embodiment of the subject matter described herein. In the embodiment illustrated in FIG. 2, the biological sample and microbubble mixture is created by adding a solution of encapsulated microbubbles to the sample (step 200) and mixing them together (step 202.) The solution of encapsulated microbubbles may be pre-prepared, or may be prepared by mixing dehydrated microbubbles with a hydrating solution that re-suspends the microbubbles and mixing the resulting solution of encapsulated microbubbles with the biological sample.

Figure 3:
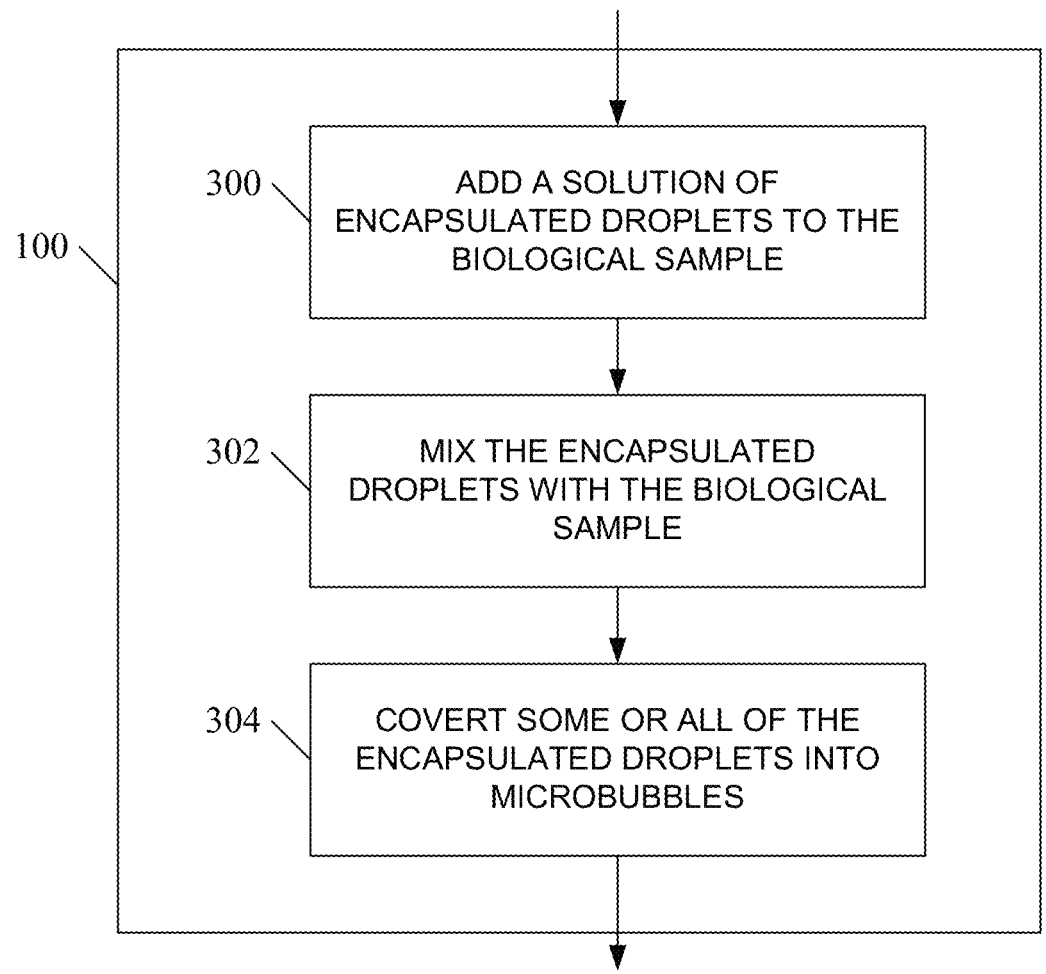
FIG. 3 is a flow chart illustrating a method for creating the biological sample and microbubble mixture according to another embodiment of the subject matter described herein.
Figure 4:
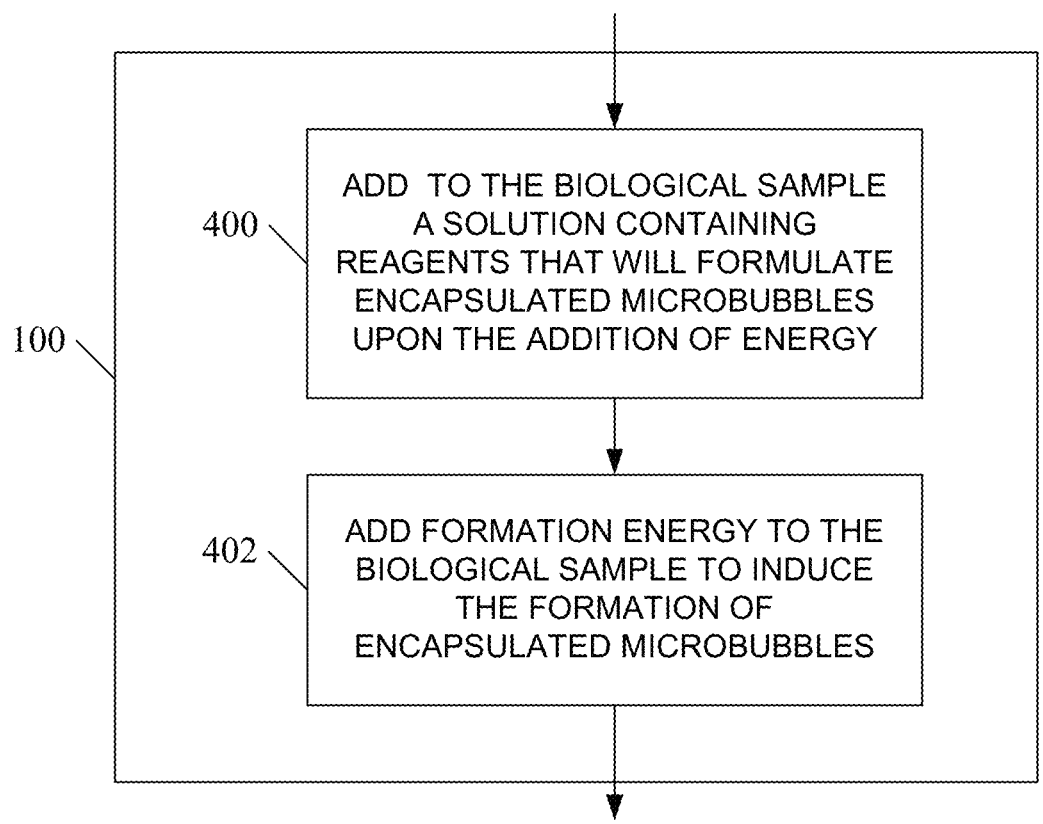
FIG. 4 is a flow chart illustrating a method for creating the biological sample and microbubble mixture according to another embodiment of the subject matter described herein.

FIG. 3 is a flow chart illustrating a method for creating the biological sample and microbubble mixture according to another embodiment of the subject matter described herein. In the embodiment illustrated in FIG. 3, the biological sample and microbubble mixture is created by adding a solution of encapsulated droplets, which may be nanodroplets, to the sample (step 300), mixing the solution with the sample (step 302), and converting at least some of the droplets to encapsulated microbubbles by the addition of conversion energy (step 303.) In one embodiment, these nanodroplets are identical in composition to the microbubbles, yet remain metastable in liquid form until the addition of acoustic energy, after which they vaporize into microbubbles.

Both standard microbubbles and vaporized phase change nanodroplets would have identical acoustically active properties once in the gas form. The benefit of the nanodroplets is that they can be prepared in sub-micron form, such as 100 to 750 nanometers, small sizes which makes them nearly neutrally buoyant and more likely to impregnate intracellular spaces for enhanced dispersion. Once vaporized, they grow in diameter by approximately a factor of 6 due to the liquid to gas volume change. The resulting bubble could play a significant role in tissue dispersion, with the additional advantage of enhanced penetration of tissue while in the liquid nanodroplet precursor stage compared to the larger and more buoyant microbubbles. The phase-change droplets have the advantage that they sink rather than float in solution, which might increase interaction with materials at the bottom of a sample chamber.

Liquid perfluorocarbon-based micro- and nano-droplets may be created with the same type of solution that is used for lipid-coated microbubbles. Microbubbles are mechanically agitated in a 3 mL vial to form a polydisperse size distribution. Due to the low boiling point of the perfluorocarbon gas, transition to the liquid phase is achievable. By increasing the pressure on the headspace of the sealed vial using a custom apparatus, the gas core will transition from the gas phase to the liquid phase, thus creating a polydisperse distribution of lipid-coated perfluorocarbon-based micro- and nano-droplets. By supplying enough acoustic energy, the droplets may transition back to the gas phase and subsequently cavitate to provide the necessary mechanism to expedite the lysis of cells.

The droplets may be converted to microbubbles before the solution is added to the biological tissue, or they may not be converted until after the solution is added to the biological tissue, which provides additional benefits in some circumstances. For example, the conversion of droplets to microbubbles after the droplets have been added to the biological tissue can effect cell lysis and can help detach tissues from a tissue culture plate in preparation for transfer to PCR plates, which may help avoid a scraping step.

In one embodiment, the droplets may include a shell surrounding a liquid core which converts to a gas upon the addition of acoustic, thermal, or optical energy. The liquid core may include a hydrocarbon or a perfluorocarbon. Examples of liquids include but are not limited to isopentane, perfluoropentane, perfluorohexane, perfluorobutane, and perfluoropropane.

Conversion energy may be added using a number of techniques, including sonicating the mixture, exposing the mixture to laser light, etc. In one embodiment, for example, the droplets may be converted into microbubbles by sonicating the mixture using ultrasound in the 0.01 MHz to 10.0 MHz frequency range.

FIG. 4 is a flow chart illustrating a method for creating the biological sample and microbubble mixture according to another embodiment of the subject matter described herein. In the embodiment illustrated in FIG. 4, the biological sample and microbubble mixture is created by adding to the biological sample a solution containing reagents that will formulate encapsulated microbubbles upon the addition of energy (step 400), then adding formation energy to a biological sample to induce the formation of encapsulated microbubbles in the biological sample (step 402.)

In one embodiment, the reagent solution may be added to the biological sample and the resulting mixture is subjected to the formulation energy, which creates the microbubbles. In one example, the reagent solution may be mixed with the biological sample and placed into a test tube or other container that contains air or some other gas. The test tube is then sealed and subjected to vigorous shaking, which creates the microbubbles. A surfactant, emulsifier, polymer, or protein may be added to the sample prior to or during the addition of the formation energy to enhance bubble stability so that the microbubbles persist until the addition of the activation energy. In another example, nanodroplets may be added to the biological sample, and the resulting mixture may be subjected to sonication or other form of formation energy, which causes the nanodroplets to vaporize into microbubbles. Sonication may include using ultrasound having a frequency in the range from 0.01 MHz to 10.0 MHz. Other types of formation energy include light, such as laser light, and heat.

All of the steps described above may be applied in parallel for the purpose of performing high throughput processing of multiple biological samples. For example, adding the solution of encapsulated microbubbles or encapsulated droplets to a sample may involve adding the solution multiple biological samples located in individual wells of a multi-well sample plate and mixing the solution with the samples in the wells. Likewise, adding the formation or activation energies may involve adding the formation or activation energies to multiple biological samples located in individual wells of a multi-well sample plate.

Figure 5A:
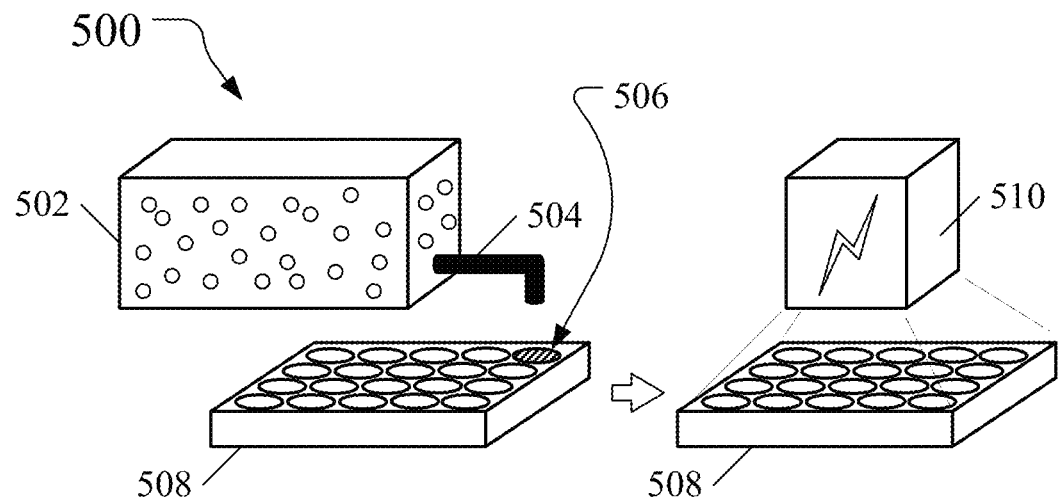
FIGS. 5A and 5B are block diagrams illustrating exemplary systems for delivering microbubbles to a biological sample according to embodiments of the subject matter described herein.

FIG. 5A illustrates a system for delivering microbubbles to a biological sample according to an embodiment of the subject matter described herein. In the embodiment illustrated in FIG. 5A, system 500 includes a container 502 for holding a solution of microbubbles, and at least one outlet 504 for delivering the solution of microbubbles to a biological sample 506. In the embodiment illustrated in FIG. 5A, biological sample 506 is contained in one or more wells of a multi-well plate 508. In one embodiment, container 502 may have multiple outlets 504 for delivering the solution of microbubbles to different wells of multi-well plate 508 in parallel for high throughput processing. In other embodiments, sample 506 may be contained in a single well plate, a test tube, or other container. In one embodiment, the solution of microbubbles may be mixed with the sample 506 in a mixing step.

In one embodiment, system 500 may include an energy source 510 for providing activation energy to the microbubbles within the sample(s) such that the microbubbles oscillate or burst and thereby process the sample. Examples of activation energy include, but are not limited to, thermal energy, sonic or ultrasonic energy, and light energy. In one embodiment, for example, activation energy may be provided using ultrasound having a frequency in the range from 0.01 MHz to 10 MHz.

System 500 may be used to perform different processes, which may be performed on different types of samples. The cavitation caused by oscillating or rupturing microbubbles can detach biological samples from a TC plate in preparation for transferal of the sample to a PCR, for example. In one embodiment, sample 506 may include DNA or DNA that has been cross-linked to protein, in which case processing sample 506 may include shearing the DNA. In another embodiment, sample 506 may include cells, such as (but not limited to) bacteria and yeast cells, in which case processing sample 506 may include effecting cell lysis. In another embodiment, sample 506 may include tissue, in which case processing sample 506 may include performing tissue dispersion. System 500 may be used to process various kinds of tissue, including fresh tissue, cryogenically preserved tissue, and fixed and paraffin embedded tissue. In one embodiment, microbubbles having a diameter in the range from 0.1 microns to 10 microns may be used for DNA shearing or other processes.

Figure 5B:
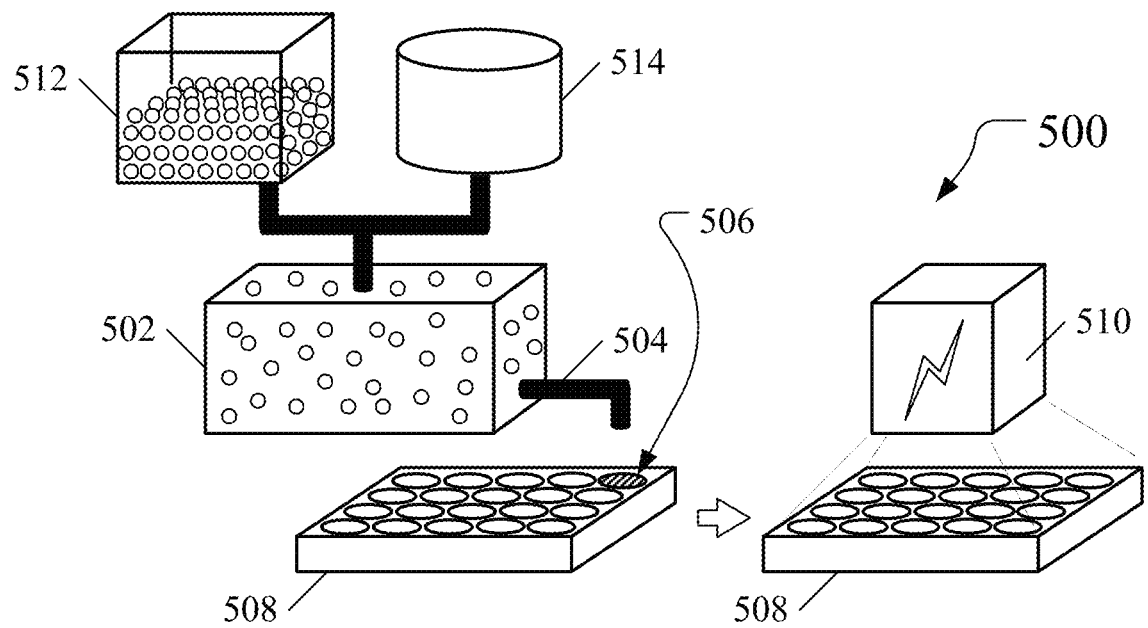

FIG. 5B illustrates a variation of system 500. In the embodiment shown in FIG. 5B, system 500 may also include a second container 512 for holding dehydrated microbubbles, which are mixed with a solution 514 and thus re-suspended before being provided to container 502.

Figure 6A:
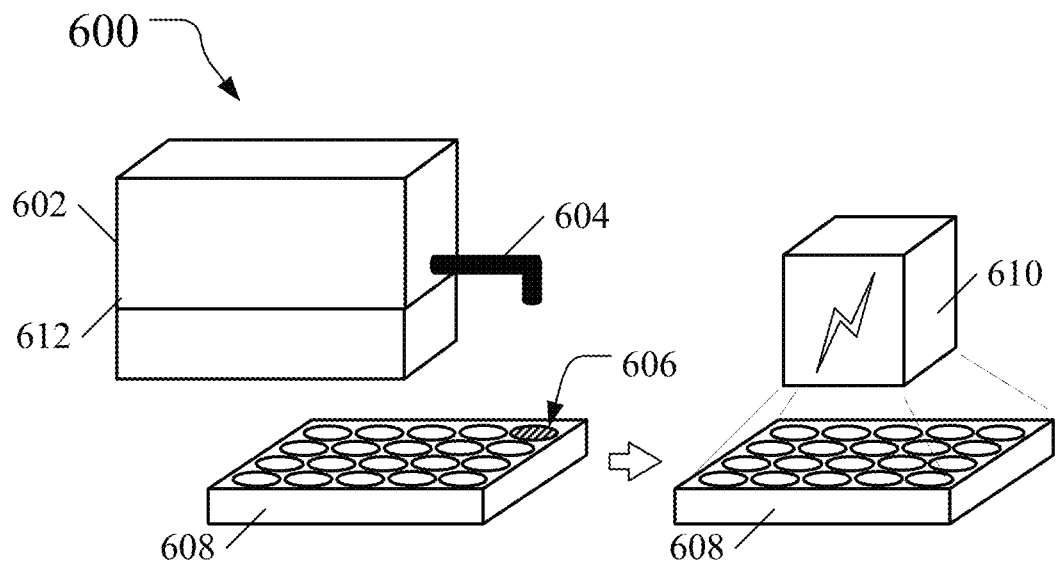
FIGS. 6A through 6F are block diagrams illustrating exemplary systems for delivering microbubbles to a biological sample according to other embodiments of the subject matter described herein.

FIG. 6A illustrates a system for delivering microbubbles to a biological sample according to an embodiment of the subject matter described herein. In the embodiment illustrated in FIG. 6A, system 600 includes a container 602 for holding a solution that will formulate encapsulated microbubbles when processed, and at least one outlet 604 for delivering the solution to a biological sample 606. In one embodiment, container 602 may have multiple outlets 604 for delivering the solution of microbubbles to different wells of multi-well plate 608 in parallel for high throughput processing. In other embodiments, sample 606 may be contained in a single well plate, a test tube, or other container. In one embodiment, the solution of microbubbles may be mixed with the sample 606 in a mixing step. In one embodiment, system 600 may include an energy source 610 for providing activation energy to the microbubbles within the sample(s) such that the microbubbles oscillate or burst and thereby process the sample. Examples of activation energy include, but are not limited to, thermal energy, sonic or ultrasonic energy, and light energy. In one embodiment, for example, activation energy may be provided using ultrasound having a frequency in the range from 0.01 MHz to 10 MHz.

Like system 500, system 600 may be used to perform different processes, which may be performed on different types of samples. The cavitation caused by oscillating or rupturing microbubbles can detach biological samples from a TC plate in preparation for transferal of the sample to a PCR, for example. In one embodiment, sample 606 may include DNA or DNA that has been cross-linked to protein, in which case processing sample 606 may include shearing the DNA. In another embodiment, sample 606 may include cells, such as (but not limited to) bacteria and yeast cells, in which case processing sample 606 may include effecting cell lysis. In another embodiment, sample 606 may include tissue, in which case processing sample 606 may include performing tissue dispersion. System 600 may be used to process various kinds of tissue, including fresh tissue, cryogenically preserved tissue, and fixed and paraffin embedded tissue. In one embodiment, microbubbles having a diameter in the range from 0.1 microns to 10 microns may be used for DNA shearing or other processes.

Unlike system 500, however, system 600 includes a microbubble-forming apparatus 612 for processing the solution to form encapsulated microbubbles within the solution. As will be described in more detail below, in one embodiment the encapsulated microbubbles are formed prior to providing the solution to sample 606 and in another embodiment the encapsulated microbubbles are formed after the solution has been provided to sample 606.

Figure 6B:
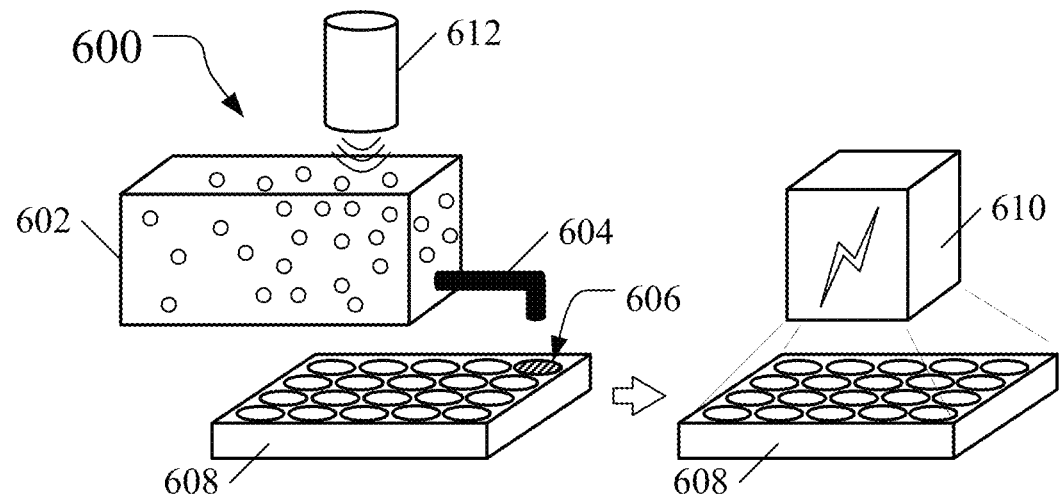

FIG. 6B illustrates a variation of system 600. In the embodiment illustrated in FIG. 6B, microbubble forming apparatus 612 includes a probe for adding sonic energy to the solution in the presence of gas to induce the formation of the microbubbles in the solution before it is added to the biological sample.

Figure 6C:
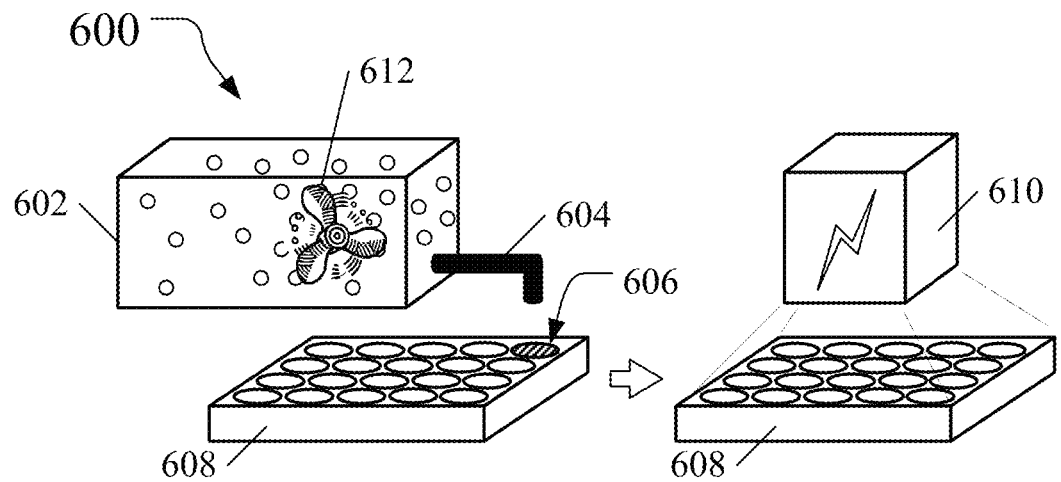

FIG. 6C illustrates another variation of system 600. In the embodiment illustrated in FIG. 6C, microbubble forming apparatus 612 includes a mechanical mixer or impeller that rapidly agitates the solution in the presence of gas, forming the microbubbles in the solution, before the solution is added to the biological sample.

Figure 6D:
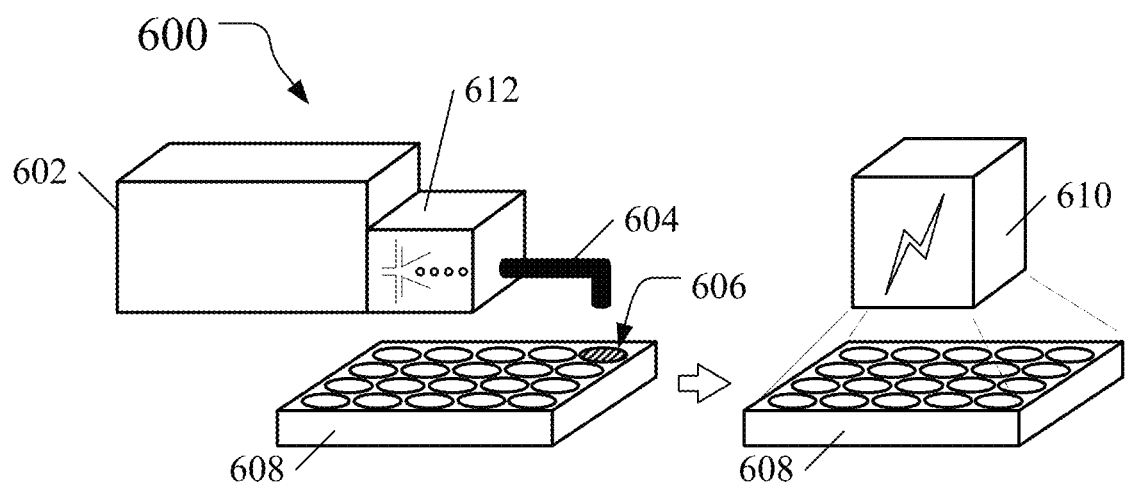

FIG. 6D illustrates yet another variation of system 600. In the embodiment illustrated in FIG. 6D, microbubble forming apparatus 612 includes one or more fluid systems that force gas surrounded by liquid through an opening or that force gas through a porous membrane, which produces microbubbles.

In one embodiment, the solution that will formulate encapsulated microbubbles when processed includes encapsulated liquid droplets or nanodroplets. In one embodiment, the droplets comprise a shell surrounding a liquid core which converts to a gas upon the addition of acoustic, thermal, or optical energy. The liquid core can include, but is not limited to including, a hydrocarbon or perfluorocarbon. In one embodiment, the liquid core includes isopentane, perfluoropentane, perfluorohexane, perfluorobutane, and/or perfluoropropane. In one embodiment, some or all of the droplets have a diameter in the range from 100 nanometers to 750 nanometers.

Figure 6E:
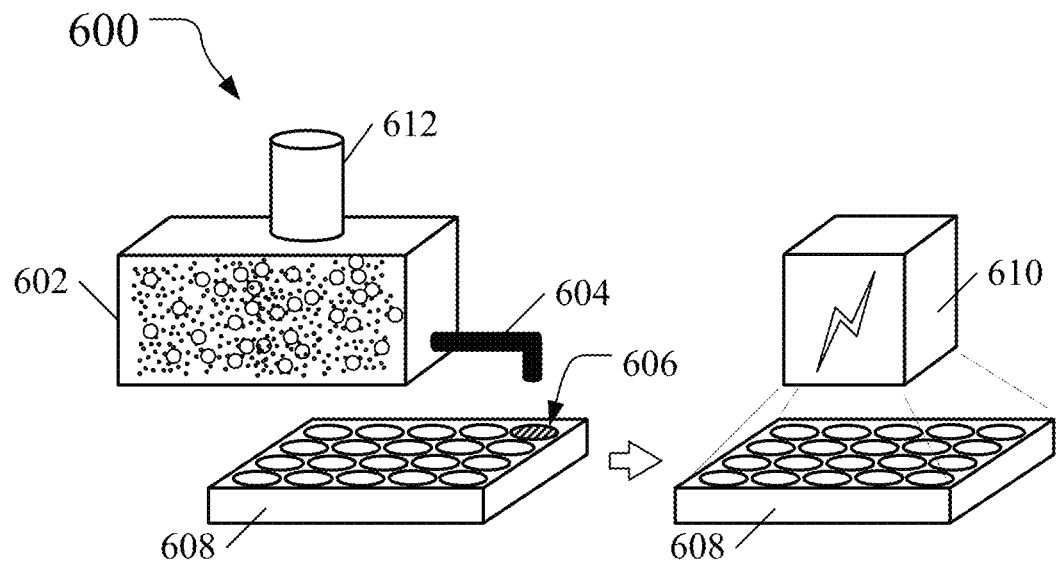
Figure 6F:
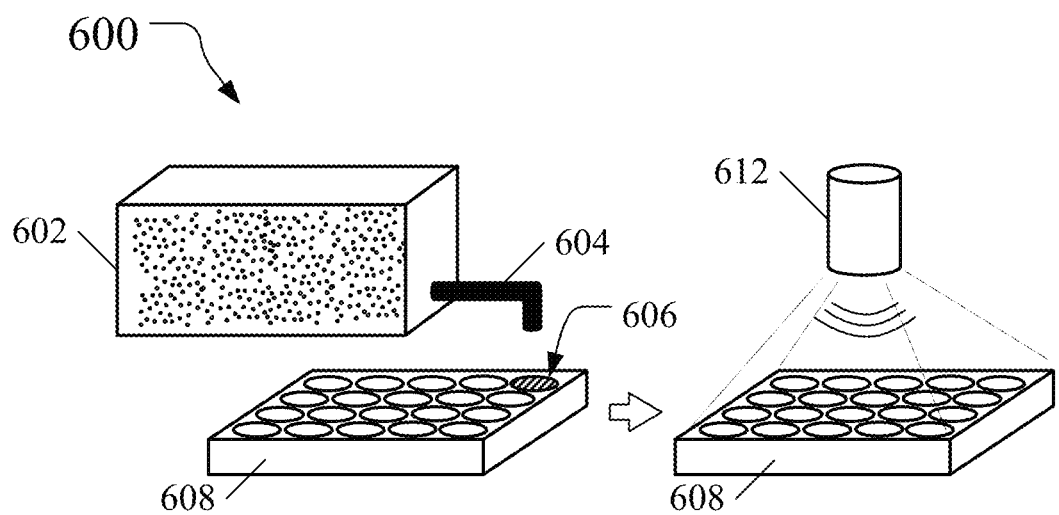

FIGS. 6E and 6F illustrate yet other variations of system 600. In the embodiments illustrated in FIGS. 6E and 6F, container 602 holds a solution that contains nanodroplets, and system 600 includes an energy source 612 for converting the droplets into microbubbles. In FIG. 6E, energy source 612 converts the droplets into microbubbles prior to mixing the resulting solution with biological sample 606.

In FIG. 6F, energy source 612 converts the droplets into microbubbles after the droplets and solution have been mixed with biological sample 606. In this manner, the expansion of the droplet into a microbubble in response to being subjected to the conversion energy provided by energy source 612 may be used to preprocess sample 606 prior to the further processing that will occur when activation energy is added to the microbubbles so created. In these embodiments, energy source 612 may be the same as or different from energy source 610, depending on what types of energy are being used for conversion and activation, respectively. In any of the embodiments illustrated herein, the solution being supplied to the biological sample may include other substances that may contribute to the creation of or stabilization of droplets or bubbles, including but not limited to surfactants, emulsifiers, polymers, or proteins.

Specific Embodiments

In one embodiment, lipid monolayer-coated microbubbles were created using 1,2-distearoyl-snglycero-3-phosphocholine (DSPC)(Avanti Polar Lipids, Alabaster, Ala.) and 1,2-distearoyl-sn-glycero-3-phosphoethanolamine-N-methoxy (polyethylene-glycol)-2000 (DSPE-PEG2000) (Avanti Polar Lipids, Alabaster, Ala.) in a 9 to 1 molar ratio as previously described. The lipids were dissolved in a buffer solution comprised of phosphate-buffered saline (PBS), propylene glycol, and glycerol (16:3:1) for a total lipid concentration of 1.0 mg/mL. The resulting lipid solution was placed into 3 mL glass vials in 1.5 mL aliquots. The vials were sealed with rubber septa and 5 capped. Finally, the air in the vial headspace was removed via a custom vacuum apparatus and replaced with decafluorobutane (Fluoromed, Round Rock, Tex.). The vial was shaken vigorously for 45 seconds using a high-speed mixer (Vialmix, Bristol-Myers Squibb Medical Imaging, North Billerica, Mass.) to produce a polydisperse distribution (Mean Diameter: 1.07±0.9, Concentration: $1.0 \times 10^{10}$ #/mL) of lipid-coated microbubbles.

Sonication was performed in a Covaris E110 sonicator in a 96-well polypropylene plate (Thermo Scientific, AB-0900). Genomic DNA (gDNA) was extracted from HEK293T cells and distributed at 10 µg per well in a final volume of 150 microliters (uL) in 10 mM Tris-HCl, pH 8.0. Our target fragment range was 300-500 base pairs (bp). Ten µL of the 1 mg/mL microbubble suspension was added to the appropriate wells. Fragmentation was confirmed by running 1 µg of DNA on a 2% agarose gel containing SYBR Green and visualizing on a Typhoon Trio+ imager.

Figure 7:
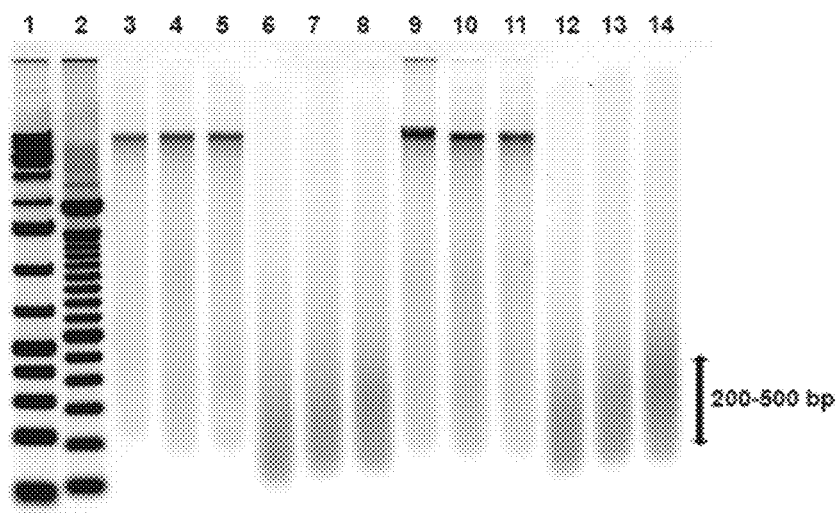
FIG. 7 shows the results of DNA fragmentation in the presence and absence of microbubbles.

FIG. 7 shows the results of DNA fragmentation in the presence and absence of microbubbles. Ten micrograms of DNA purified from human HEK293T cells was resuspended in 150 uL final volume per well of a 96-well plate and sonicated in a Covaris E110 sonicator for 30 seconds (Lanes 3-8) or 1 minute (Lanes 9-14) in triplicate. DNA fragmentation without any additive is inefficient (Lanes 3-5 and 9-11). Addition of 10 uL of one micron lipid encapsulated microbubbles significantly increased the efficiency of fragmentation (Lanes 6-8 and 12-14). DNA ladders are: 1 Kb plus (Fermentas, Lane 1), and 100 bp (Invitrogen, Lane 2). This image represents one of three biological replicates. The samples with microbubbles were efficiently sheared to the desired 300-500 bp range within 30 seconds (Lanes 6-8), while the samples without microbubbles showed very little fragmentation (Lanes 3-5 and 6-8).

Figure 8:
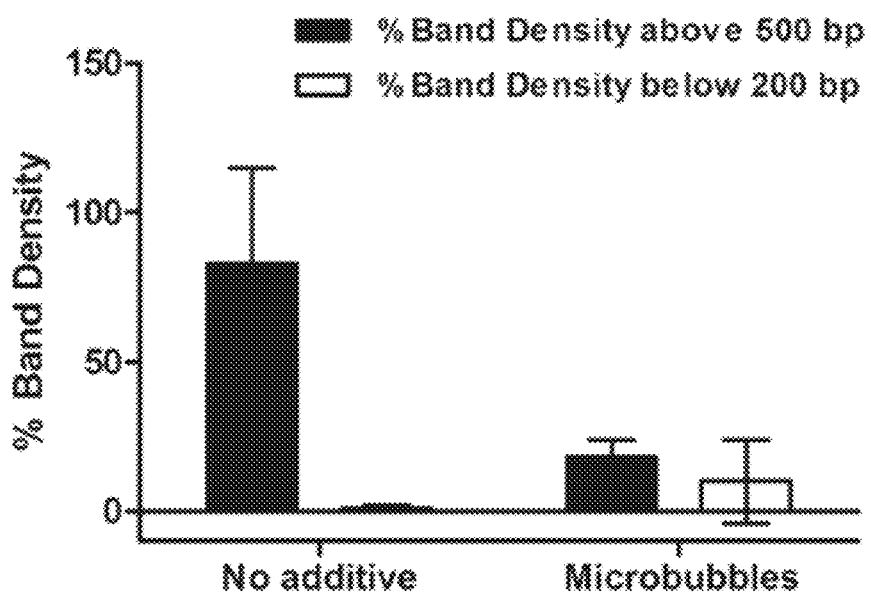
FIG. 8 shows the results of densitometry performed on three independent biological replicates after 30 seconds sonication time.

FIG. 8 shows the results of densitometry performed on three independent biological replicates after 30 seconds sonication time. Densitometry analysis indicates that DNA fragmentation is centered in the 200-500 bp range for samples sonicated for 30 seconds in the presence of lipid-encapsulated microbubbles. Percent band density was calculated using the rolling ball method (ImageQuant TL, GE) by dividing the density for the indicated size range by the density for the entire lane. Error bars represent the standard deviation for 3 biological replicates with 3 technical replicates each. The addition of microbubble reagent to the acoustic sonication process significantly improved the consistency of DNA fragmentation by producing fragments within a narrow size distribution.

Analysis to assess DNA integrity confirmed that the presence of microbubbles does not interfere with downstream fluorescent-based analyses. Three biological replicates of gDNA fragmented in the presence of microbubbles from FIG. 7 were removed from the sonication vessel and directly used for qPCR using a SYBR green master mix and the absolute quantification method with primers representing various genomic loci. When compared to a standard curve of unsonicated human genomic DNA, 10-fold serial dilutions of fragmented DNA could be linearly amplified. The PCR products were subjected to dissociation curve analysis to confirm that only a single PCR product was present. Both the standards, and the microbubble fragmented DNA produced a single amplification product. In short, it was confirmed that the presence of lipid microbubbles in the fragmented DNA does not interfere with SYBR green-based qPCR analysis.

Overall, the addition of microbubbles to the DNA fragmentation process is an innovative approach that allows purified gDNA to be consistently fragmented in a manner of seconds. The same techniques may be applied to extraction and fragmentation of DNA from formalin fixed paraffin embedded (FFPE) tissue slices and cryopreserved biopsy samples. The short sonication times that are possible with microbubble addition could greatly improve sample integrity by decreasing sample handling while increasing processing efficiency and robustness.

An Example DNA Shearing Protocol:
1. Grow human cell line on 10 cm plates (~1-3×10^6 cells per plate).
2. For formaldehyde fixed cells, fix cells with 1% formaldehyde at room temperature with gentle shaking for 5 minutes. For non-fixed cells, proceed directly to step 4.
3. Stop cross-linking reaction with 125 mM glycine for 5 minutes at room temperature with gentle shaking.
4. Wash cells on ice 2 times with 10 mL phosphate buffered saline, pH 7.5 (PBS).
5. Scrape cells into 1 mL PBS, transfer to 1.7 mL tube, and centrifuge at 500×g for 5 minutes. Remove supernatant.
6. Wash plates with 1 mL PBS, scrape again, and add to tubes with pellets. Centrifuge at 500×g for 5 minutes in Eppendorf 5430 table top centrifuge. Remove supernatant.
7. Flash-freeze pellets in liquid nitrogen. Store at −80 C until needed. Each pellet contains ~1×10^6 cells.
8. Re-suspend cell pellet in 150 uL lysis buffer (10 mM Tris, pH 8.0/100 mM NaCl/1 mM EDTA/2% Triton X-100/1% SDS) with 1× protease inhibitor cocktail (Roche #05056489001).
9. Transfer 150 uL of cell suspension to one well of a 96-well PCR plate (ABgene #SP-0410).
10. Add 10 uL of polydispersed mechanically agitated lipid microbubbles to each well.
11. Seal plate with heat sealer.
12. Sonication is performed using a Covaris model E110 acoustic sonicator. Sonicate each well for 1 minute using the following settings: 20% duty cycle/8 intensity/200 cycles per burst.
13. Remove cover. Add 10 uL more of polydispersed lipid microbubbles to each well.
14. Seal plate with heat sealer.
15. Sonicate each well for 4 minutes using the following settings: 20% duty cycle/8 intensity/200 cycles per burst.
16. Centrifuge plate at 1,300× g (1,500 rpm) for 5 minutes at 4 C to remove crude cellular debris.
17. Remove seal.
18. Transfer sonicated lysates to 1.7 mL tubes. Centrifuge at high speed for one minute to pellet cell debris.
19. Transfer 10 uL from each tube to a fresh tube. Add 190 uL TE, pH 8.0 and 2 uL 5 mg/mL RNase. Incubate tubes at 37 C for 1 hour. Add 200 uL 2× proteinase K buffer (50 mM Tris, pH 8.0/12.5 mM EDTA, pH 8.0/300 mM NaCl/1% SDS) and 2 uL 10 mg/mL proteinase K. Incubate at 55 C overnight. Extract samples by phenol:chloroform and confirm fragment size by gel electrophoresis.
20. Use the remaining 140 uL sonicated DNA in downstream applications.

An Example Ablation Process:
1. Removal of formaldehyde cross-linked cells from a 96-well tissue culture plate. Once cells have been formaldehyde cross-linked, they are particularly difficult to remove from a surface without manual scraping. To remove these cells we will do the following:
    a. Add formaldehyde to 1% directly to the cell culture media in each well of a 96-well plate for 5 minutes followed by the addition of glycine to 125 mM final concentration to stop crosslinking reaction.
    b. Wash cells with PBS. Add 150 uL lysis buffer (10 mM Tris, pH 8.0/100 mM NaCl/1 mM EDTA/2% Triton X-100/1% SDS) with 1× protease inhibitor cocktail (Roche #05056489001).
    c. Add 100 uL (Not sure about the exact amount) of lipid-coated perfluorocarbon droplets. The droplets sink to the bottom of the well where the fixed cells are located. Seal plate.
    d. Place plate in Covaris E110 sonicator. Sonicate for 1 minute per well.
    e. Remove seal, transfer resuspended cells to 96-well PCR plate (ABGene #SP-0410). Proceed with sonication as described in Step #13 in tested protocol, above. The droplets will "activate," by vaporizing and subsequently cavitate in the presence of sonication.

Other Permutations:
Use of microbubbles with polymer or protein shells
Use of microbubbles with different gas cores—such as oxygen, air, or different perfluorocarbons
Use of phase-change droplets which convert to microbubbles upon acoustic energy
Use of microbubbles with different sizes
Use of varying acoustic energies, duty cycles, and frequencies to optimize interaction with microbubbles
Use of microfluidics systems to produce the microbubbles directly at the site of use Other Embodiments Other embodiments contemplated by the subject matter described herein include, but are not limited to, the following list:
1. A method for using encapsulated microbubbles to process a biological sample, the method comprising: adding a pre-prepared solution of encapsulated microbubbles to a biological sample; creating a mixture by mixing the pre-prepared solution of encapsulated microbubbles with the biological sample; and adding energy to the mixture to cause at least some of the microbubbles to oscillate and/or burst and thereby process the sample.
2. The method of list item 1 wherein the biological sample comprises DNA or DNA that has been cross linked to protein and wherein processing the sample comprises shearing the DNA.
3. The method of list item 1 wherein the biological sample comprises cells and wherein processing the sample comprises effecting cell lysis.
4. The method of list item 3 wherein the cells comprise bacteria or yeast cells.
5. The method of list item 1 wherein the sample comprises tissue, and wherein processing the sample comprises performing tissue dispersion.
6. The method of list item 5 wherein the tissue is fresh, or cryogenically preserved, or fixed and paraffin embedded
The method of list item 1 wherein adding energy to the mixture comprises sonicating the mixture
8. The method of list item 7 wherein sonicating the mixture includes applying energy of a frequency between 0.01 MHz and 10.0 MHz.
9. The method of list item 1 wherein adding energy to the mixture comprises exposing the sample to laser light
10. The method of list item 1 wherein adding a pre-prepared solution of encapsulated microbubbles to a simple includes adding the solution to a plurality of biological samples located in individual wells of a multi-well sample plate, wherein mixing the pre-prepared solution includes mixing the solution with the samples in the wells, and wherein adding energy to the mixtures includes adding the energy to each of the mixtures in the wells to perform high throughput processing of a plurality of biological samples.

11. The method of list item 1 wherein a majority of the microbubbles are between 0.1 microns and 10 microns in diameter.

12. A method for using encapsulated droplets to process a biological sample, the method comprising: adding a pre-prepared solution of encapsulated droplets to a biological sample; creating a mixture by mixing the pre-prepared solution of encapsulated droplets with the biological sample; and adding energy to the mixture to convert at least some of the droplets to gas bubbles, and adding further energy to the gas bubbles to oscillate and/or burst the gas bubbles, and thereby process the sample.

13. The method of list item 12 wherein the droplets consist of a shell surrounding a liquid core which converts to a gas upon the addition of acoustic, thermal, or optical energy.

14. The method of list item 13 wherein the liquid core includes a hydrocarbon or a perfluorocarbon.

15. The system of list item 14 wherein the liquid core includes isopentane, perfluoropentane, perfluorohexane, perfluorobutane, or perfluoropropane.

16. The method of list item 12 wherein the biological sample comprises DNA or DNA that has been cross linked to protein, and wherein processing the sample comprises shearing the DNA.

17. The method of list item 12 wherein the biological sample comprises cells and wherein processing the sample comprises effecting cell lysis 18. The method of list item 17 wherein the cells comprise bacteria or yeast cells.

19. The method of list item 12 wherein the sample comprises tissue and wherein processing the sample comprises performing tissue dispersion.

20. The method of list item 12 wherein the tissue is fresh, or cryogenically preserved, or fixed and paraffin embedded 21. The method of list item 12 wherein adding energy to the mixture comprises sonicating the mixture.

22. The method of list item 21 wherein sonicating the mixture includes adding energy having a frequency range from 0.01 MHz and 10.0 MHz.

23. The method of list item 12 wherein adding energy to the mixture comprises exposing the sample to laser light.

24. The method of list item 12 wherein adding a pre-prepared solution of encapsulated droplets to a sample includes applying the solution to a plurality of biological samples located in individual wells of a multi-well sample plate, wherein mixing the pre-prepared solution includes mixing the solution with the samples in the wells and wherein adding energy to the mixture includes adding energy to the mixtures in the wells to perform high throughput processing of a plurality of biological samples.

25. The method of list item 12 where a majority of droplets are between 0.1 and 10 microns in diameter.

26. A method for using encapsulated microbubbles to process a biological sample, the method comprising: adding first energy to a biological sample to first induce the formation of encapsulated microbubbles in the biological sample; and adding second energy to the sample to oscillate and/or burst the microbubbles and thereby process the sample.

27. The method of list item 26 comprising adding a surfactant, emulsifier, polymer, or protein to the biological sample prior to or during the addition of the first energy to enhance bubble stability so that the microbubbles persist until the addition of the second energy.

28. the method of list item 26 where droplets of liquid are added to the biological sample, prior to or during the addition of first energy, so that said liquid droplets vaporize into bubbles during administration of first energy, and resulting bubbles which oscillate and/or burst in response to the addition of the second energy.

29. The method of list item 26 wherein adding energy to the sample to induce the formation of encapsulated microbubbles includes applying laser light to the sample to form the microbubbles.

30. The method of list item 26 wherein adding energy to the sample to induce the formation of encapsulated microbubbles includes sonicating the sample to form the microbubbles.

31. The method of list item 30 wherein sonicating the sample includes applying sonic energy of a frequency 0.01 and 10.0 MHz.

32. The method of list item 26 wherein the biological sample comprises
DNA or DNA that has been cross linked to protein and wherein processing the sample comprises shearing the DNA.

33. The method of list item 26 wherein the biological sample comprises cells and wherein processing the sample comprises effecting cell lysis.

34. The method of list item 33 wherein the cells comprise bacteria or yeast cells.

35. The method of list item 26 wherein the sample comprises tissue and wherein processing the sample comprises performing tissue dispersion.

36. The method of list item 35 wherein the tissue is fresh, or cryogenically preserved, or fixed and paraffin embedded 37. The method of list item 26 wherein adding the first and second energies to a biological sample includes adding the first and second energies to a plurality of biological samples located in individual wells of a multi-well sample plate to perform high throughput processing of a plurality of biological samples.

38. A system for delivering a solution for delivering microbubbles to a biological sample, the system comprising: a container for holding a solution, the solution comprising reagents that will formulate encapsulated microbubbles upon the addition of energy; and at least one outlet for delivering the pre-prepared solution of to a biological sample.

39. The system of list item 38 comprising a probe for adding sonic energy to the solution in the presence of gas to induce the formation of the microbubbles in the solution before it is added to the biological sample.

40. The system of list item 38 comprising a mechanical mixer/impeller that rapidly agitates the solution in the presence of gas, forming the microbubbles in the solution, before the solution is added to the biological sample.

41. The system of list item 38 comprising at least one fluid system which forces gas surrounded by liquid through an opening to result in microbubble production.

42. The system of list item 38 comprising at least one fluid system that forces gas through a porous membrane to form the microbubbles.

43. The system of list item 38 wherein the biological sample will then be exposed to additional thermal, sonic, or light energy for processing.

44. The system of list item 43 wherein the additional energy is ultrasound with a frequency between 0.01 to 10 MHz.

45. The system of list item 38 wherein the biological sample comprises DNA or DNA that has been cross linked to protein and wherein processing the sample comprises shearing the DNA.
46. The system of list item 38 wherein the biological sample comprises cells and wherein processing the sample comprises effecting cell lysis.
47. The system of list item 46 wherein the cells comprise bacteria or yeast cells.
48. The system of list item 38 wherein the sample comprises tissue and wherein processing the sample comprises performing tissue dispersion.
49. The system of list item 48 wherein the tissue is fresh, or cryogenically preserved, or fixed and paraffin embedded
50. The system of list item 38 wherein the container includes a plurality of outlets for delivering the solution of microbubbles to different wells of a multi-well plate.
51. The system of list item 38 where the solution of reagents includes surfactants, emulsifiers, polymers, or proteins
52. A system for delivering a pre-prepared solution of microbubbles to a biological sample, the system comprising: a container for holding the solution of microbubbles; and at least one outlet for delivering the pre-prepared solution of microbubbles to a biological sample.
53. The system of list item 52 comprising an energy source for exposing the biological sample to thermal, sonic, or light energy for processing
54. The system of list item 53 wherein the additional energy is ultrasound with a frequency between 0.01 to 10 MHz.
55. The system of list item 52 wherein the biological sample comprises
DNA or DNA that has been cross linked to protein and wherein processing the sample comprises shearing the DNA.
56. The system of list item 52 wherein the biological sample comprises cells and wherein processing the sample comprises effecting cell lysis.
57. The system of list item 56 wherein the cells comprise bacteria or yeast cells.
58. The system of list item 52 wherein the sample comprises tissue and wherein processing the sample comprises performing tissue dispersion.
59. The system of list item 58 wherein the tissue is fresh, or cryogenically preserved, or fixed and paraffin embedded
60. The system of list item 52 wherein the container includes a plurality of outlets for delivering the solution of microbubbles to different wells of a multi-well plate.
61. The system of list item 52 wherein a majority of the microbubbles are between 0.1 and 10 microns in diameter.
62. A system for delivering a pre-prepared solution of encapsulated liquid droplets to a biological sample, the system comprising: a container for holding the solution of encapsulated liquid droplets; and at least one outlet for delivering the pre-prepared solution of encapsulated liquid droplets to a biological sample.
63. The system of list item 62 where the droplet consists of a shell surrounding a liquid core which converts to a gas upon the addition of acoustic, thermal, or optical energy.
64. The system of list item 63 where the liquid core is a hydrocarbon or perfluorocarbon.
65. The system of list item 64 wherein the liquid core comprises isopentane, perfluoropentane, perfluorohexane, perfluorobutane, or perfluoropropane.
66. The system of list item 62 comprising an energy source for adding thermal, sonic, or light energy to the sample for processing.
67. The system of list item 66 wherein the additional energy is ultrasound with a frequency between 0.01 to 10 MHz.
68. The system of list item 62 wherein the biological sample comprises DNA or DNA that has been cross linked to protein and wherein processing the sample comprises shearing the DNA.
69. The system of list item 62 wherein the biological sample comprises cells and wherein processing the sample comprises effecting cell lysis.
70. The system of list item 69 wherein the cells comprise bacteria or yeast cells.
71. The system of list item 62 wherein the sample comprises tissue and wherein processing the sample comprises performing tissue dispersion.
72. The method of list item 71 wherein the tissue is fresh, or cryogenically preserved, or fixed and paraffin embedded.
73. The system of list item 62 wherein the container includes a plurality of outlets for delivering the solution of encapsulated liquid droplets to different wells of a multi-well plate.
74. The system of list item 62 wherein a majority of encapsulated liquid droplets are between 0.1 and 10 microns in diameter.
75. A system for delivering a pre-prepared solution of microbubbles to a biological sample, the system comprising: a container which holds dehydrated microbubbles which are mixed with a solution and thus resuspended; and at least one outlet for delivering the resuspended microbubbles to a biological sample.
76. The system of list item 75 wherein the biological sample will then be exposed to additional thermal, sonic, or light energy for processing
77. The system of list item 76 wherein the additional energy is ultrasound with a frequency between 0.01 to 10 MHz.
78. The system of list item 75 wherein the biological sample comprises DNA or DNA that has been cross linked to protein and wherein processing the sample comprises shearing the DNA.
79. The system of list item 75 wherein the biological sample comprises cells and wherein processing the sample comprises effecting cell lysis.
80. The system of list item 75 wherein the cells comprise bacteria or yeast cells.
81. The system of list item 75 wherein the sample comprises tissue and wherein processing the sample comprises performing tissue dispersion.
82. The method of list item 81 wherein the tissue is fresh, or cryogenically preserved, or fixed and paraffin embedded.
83. The system of list item 75 wherein the container includes a plurality of outlets for delivering the solution of encapsulated liquid droplets to different wells of a multi-well plate.
84. The system of list item 75 wherein a majority of the microbubbles are between 0.1 and 10 microns in diameter.

It will be understood that various details of the subject matter described herein may be changed without departing from the scope of the subject matter described herein. Furthermore, the foregoing description is for the purpose of illustration only, and not for the purpose of limitation.

What is claimed is:

1. A method for using encapsulated microbubbles to process a biological sample to shear and extract random, unbiased DNA fragments from the sample, the method comprising:
creating a mixture comprising encapsulated nanodroplets mixed with a biological sample comprising DNA, wherein creating the mixture comprises adding a solution of encapsulated nanodroplets to the sample and mixing the solution with the sample;

adding energy to the mixture to cause at least some of the nanodroplets to form encapsulated microbubbles, which oscillate or burst and thereby process the sample and shear the DNA, and extracting the sheared, random, and unbiased DNA fragments from the sample.

2. The method of claim 1 wherein a majority of the encapsulated microbubbles have a diameter in the range from 0.1 microns to 10 microns.

3. The method of claim 1 wherein the biological sample comprises cells and wherein processing the sample comprises effecting cell lysis.

4. The method of claim 3 wherein the cells comprise cells from a tissue culture, bacteria cells, or yeast cells.

5. The method of claim 1 wherein the sample comprises tissue and wherein processing the sample comprises performing tissue dispersion.

6. The method of claim 1 wherein the sample comprises at least one of fresh tissue, cryogenically preserved tissue, and fixed and paraffin embedded tissue.

7. The method of claim 6 wherein the sample comprises fixed and paraffin embedded tissue.

8. The method of claim 1 wherein adding the energy to the mixture comprises sonicating the mixture.

9. The method of claim 8 wherein sonicating the mixture includes applying energy having a frequency in the range from 0.01 MHz to 10.0 MHz.

10. The method of claim 1 wherein adding the energy to the mixture comprises exposing the mixture to laser light.

11. The method of claim 1 wherein the nanodroplets comprise a shell surrounding a liquid core which converts to a gas upon the addition of the energy, wherein the energy comprises at least one of acoustic, thermal, and optical energy.

12. The method of claim 11 wherein the liquid core comprises a hydrocarbon or a perfluorocarbon.

13. The method of claim 12 wherein the liquid core comprises at least one of isopentane, perfluoropentane, perfluorohexane, perfluorobutane, and perfluoropropane.

14. The method of claim 1 wherein a majority of nanodroplets have a diameter in the range from 100 to 750 nanometers.

15. The method of claim 1 wherein adding the energy comprises adding formation energy to a biological sample to induce the formation of encapsulated microbubbles in the biological sample and adding activation energy to cause at least some of the microbubbles to oscillate or burst.

16. The method of claim 15 wherein creating the mixture comprises adding a surfactant, emulsifier, polymer, or protein to the sample prior to or during the addition of the formation energy to enhance bubble stability so that the microbubbles persist until the addition of activation energy.

17. The method of claim 15 wherein creating the mixture comprises adding the nanodroplets to the sample prior to or during the addition of the formation energy, wherein, during administration of formation energy, at least some of the nanodroplets vaporize into the bubbles that will oscillate or burst in response to the addition of activation energy.

18. The method of claim 15 wherein adding the formation energy comprises applying laser light to the sample to form the microbubbles.

19. The method of claim 15 wherein adding the formation energy includes sonicating the sample to form the microbubbles.

20. The method of claim 19 wherein sonicating the sample includes applying sonic energy having a frequency in the range from 0.01 MHz to 10.0 MHz.

21. The method of claim 1 wherein adding the solution of encapsulated nanodroplets to the sample comprises adding the solution to a plurality of biological samples located in individual wells of a multi-well sample plate, wherein mixing the solution includes mixing the solution with the samples in the wells wherein adding the energy to the mixture includes adding the energy to each of the mixtures in the wells to perform high throughput processing of a plurality of biological samples.

* * * * *